United States Patent
Jain et al.

(10) Patent No.: US 11,058,713 B2
(45) Date of Patent: Jul. 13, 2021

(54) TREATMENT AND DIAGNOSIS OF OCULAR SURFACE DISORDERS

(71) Applicant: Advaite LLC., Chicago, IL (US)

(72) Inventors: Sandeep Jain, Oak Park, IL (US); Karthik Musunuri, Chester Springs, PA (US)

(73) Assignee: ADVAITE LLC., Chicago, IL (US)

( * ) Notice: Subject to any disclaimer, the term of this patent is extended or adjusted under 35 U.S.C. 154(b) by 15 days.

(21) Appl. No.: 15/909,239

(22) Filed: Mar. 1, 2018

(65) Prior Publication Data

US 2019/0000871 A1 Jan. 3, 2019

Related U.S. Application Data

(60) Provisional application No. 62/526,891, filed on Jun. 29, 2017, provisional application No. 62/575,508, filed on Oct. 22, 2017.

(51) Int. Cl.
*A61K 31/727* (2006.01)
*A61P 27/02* (2006.01)
*A61K 45/06* (2006.01)

(52) U.S. Cl.
CPC ............ *A61K 31/727* (2013.01); *A61K 45/06* (2013.01); *A61P 27/02* (2018.01)

(58) Field of Classification Search
None
See application file for complete search history.

(56) References Cited

U.S. PATENT DOCUMENTS

| | | | |
|---|---|---|---|
| 6,624,193 B1* | 9/2003 | Naka .................... | A61K 31/222 514/546 |
| 2004/0018996 A1* | 1/2004 | Richardson .......... | A61K 9/0034 514/42 |
| 2005/0043271 A1* | 2/2005 | Gross .................... | A61K 31/727 514/54 |
| 2006/0122152 A1* | 6/2006 | Peyman ................. | A61K 31/65 514/56 |
| 2009/0253661 A1* | 10/2009 | Peyman ................. | A61K 31/65 514/154 |
| 2015/0010524 A1* | 1/2015 | Jain ....................... | A61K 9/0048 424/94.6 |
| 2016/0114013 A1* | 4/2016 | Pokushalov .......... | A61K 47/36 424/94.67 |
| 2018/0177924 A1* | 6/2018 | Difiore .................. | A61K 9/0048 |

FOREIGN PATENT DOCUMENTS

| | | | | |
|---|---|---|---|---|
| GB | 2207049 A | * | 1/1989 | ............ A61K 9/0048 |
| WO | WO-2017148951 A1 | * | 9/2017 | ............ G16H 50/30 |

OTHER PUBLICATIONS

Cohen-Mazor, M., Mazor, R., Kristal, B., Kistler, E. B., Ziv, I., Chezar, J., & Sela, S. (2015). Heparin interaction with the primed polymorphonuclear leukocyte cd11b induces apoptosis and prevents cell activation. Journal of immunology research, 2015. (Year: 2015).*

Salom, D., Sanz-Marco, E., Mullor, J. L., Lopez-Prats, M. J., Garcia-Delpech, S., Udaondo, P., . . . & Diaz-Llopis, M. (2010). Aqueous humor neutrophil gelatinase-associated lipocalin levels in patients with idiopathic acute anterior uveitis. Molecular vision, 16, 1448. (Year: 2010).*

María Jesús Benito, María J. González-García, Marisa Tesón, Noelia García, Itziar Fernández, Margarita Calonge, Amalia Enríquez-de-Salamanca. Intra- and inter-day variation of cytokines and chemokines in tears of healthy subjects, Experimental Eye Research, vol. 120,2014,pp. 43-49. (Year: 2014).*

Liu, Jian-Wei,., Xiu-Yun, L., & Ai-Jun, D. (2017). Effectiveness of heparin eye drops in paraquat-induced ocular injury. Cutaneous and ocular toxicology, 36(4), 377-380. (Year: 2017).*

Duran, J. A., Malvar, A., Rodriguez-Ares, M. T., & Garcia-Riestra, C. (1993). Heparin inhibits Pseudomonas adherence to soft contact lenses. Eye, 7(1), 152-154. (Year: 1993).*

Zaturinsky, B., Naveh, N., Saks, D., & Solomon, A. S. (1990). Prevention of posterior capsular opacification by cryolysis and the use of heparinized irrigating solution during extracapsular lens extraction in rabbits. Ophthalmic Surgery, Lasers and Imaging Retina, 21 (6), 431-434. (Year: 1990).*

* cited by examiner

*Primary Examiner* — Dale R Miller
(74) *Attorney, Agent, or Firm* — Don D. Cha; HDC Intellectual Property Law, LLP

(57) ABSTRACT

The present invention provides an ophthalmic formulation consisting essentially of one or more pharmaceutically acceptable excipients; a pharmaceutically active compound that is capable of reducing the amount of inflammatory neutrophil product on the ocular surface; and optionally a second pharmaceutically active compound selected from the group consisting of a steroid, an anti-inflammatory agent, a mucolytic agent and a combination thereof. In particular, the present invention provides an ophthalmic formulation where the pharmaceutically active compound is capable of treating a clinical condition selected from the group consisting of inflammatory and immunological ocular surface disease that can cause symptoms of ocular discomfort, mucocellular aggregates/debris in tear film, symblepheron formation, fornix foreshortening, eyelid margin/conjunctival keratinization, corneal neovascularization/pannus, subconjunctival fibrosis, and herpetic eye disease. The present invention also provides a method for diagnosing or monitoring an ocular surface disease.

6 Claims, 11 Drawing Sheets

TREATMENT AND DIAGNOSIS OF OCULAR SURFACE DISORDERS

CROSS-REFERENCE TO RELATED APPLICATIONS

This application claims the priority benefit of U.S. Provisional Application Nos. 62/526,891, filed Jun. 29, 2017, and 62/575,508, filed Oct. 22, 2017, all of which are incorporated herein by reference in their entirety.

STATEMENT REGARDING FEDERALLY FUNDED RESEARCH

This invention was made with government support under grant number RO1 EY024966 awarded by the National Eye Institute (NEI)/National Institutes of Health (NIH). The government has certain rights in the invention.

FIELD OF THE INVENTION

The present invention relates to an ophthalmic formulation consisting essentially of one or more pharmaceutically acceptable ophthalmic excipients; a pharmaceutically active compound that is capable of reducing the amount of inflammatory neutrophil product on the ocular surface; and optionally a second pharmaceutically active compound selected from the group consisting of a steroid, an anti-inflammatory agent, a mucolytic agent and a combination thereof. In another formulation, the pharmaceutically active compound is capable of treating a clinical condition selected from the group consisting of inflammatory and immunological ocular surface disease that can cause symptoms of ocular discomfort, mucocellular aggregates/debris in tear film, symblepheron formation, fornix foreshortening, eyelid margin/conjunctival keratinization, corneal neovascularization/pannus and subconjunctival fibrosis. The present invention also relates to a method for using the ophthalmic formulation disclosed herein to treat such a clinical condition.

BACKGROUND OF THE INVENTION

Inflammatory and immunological ocular surface diseases can cause various symptoms including, but not limited to, ocular discomfort, a dry eye syndrome, mucocellular aggregates/debris in tear film, symblepheron formation, fornix foreshortening, eyelid margin/conjunctival keratinization, corneal neovascularization/pannus and subconjunctival fibrosis. More specific types of ocular surface diseases include ocular graft-versus-host disease (oGVHD), Steven Johnson syndrome, ocular cicatricial pemphigoid (OCP), mild, moderate and severe tear deficient dry eye disease (DED), meibomian gland disease, superior limbic keratoconjunctivitis (SLK), tear sufficient DED, floppy eyelid syndrome, neurotrophic eye disease, aniridia, a postoperative/post-trauma ocular condition, and herpetic eye disease (e.g., herpes zoster ophthalmicus and herpes simplex keratitis).

Conventional treatments for some of these ocular surface diseases, in particular dry eye syndrome, include (i) instillation of artificial tears for tear supplementation and stimulation and (ii) the use of anti-inflammatory drugs to reduce ocular surface inflammation. Generally, current dry eye treatment involves topical application of artificial tear products/lubricants, tear retention management, stimulation of tear secretion, topical application of antibiotics (e.g., erythromycin or bacitracin ointments), oral administration of tetracyclines (e.g., tetracycline, doxycycline, or minocycline), application of anti-inflammatory compounds and corticosteroids. These treatments are often time consuming, frustrating, and frequently ineffective or variably effective. Moreover, while conventional treatment is effective in reducing symptoms of dry eye syndrome to some extent, it has many undesired side effects, such as burning and stinging sensations. To decrease local side effects and to enhance the patient's comfort is one of the objectives of the present invention.

Another shortcoming of conventional treatment in ocular surface disease treatment is inconsistent uptake of active pharmaceutical ingredients into corneal cells and their resident time in the cornea to effectively treat ocular surface disease syndrome without continual application. While ointment or cream formulations may allow longer residence time, such formulations may not disrupt the stratum corneum (superficial cornified layers of skin) and may not reach the blood vessels and nerves that are present deeper in the eyelid tissue.

Yet another problem associated with conventional treatment is that no underlying cause has been directly addressed. Discovering the cause of ocular surface diseases allows more effective treatment. Conventional treatments, for most part, treat only the symptoms of ocular surface disease.

Accordingly, there is a continuing need for compositions and methods for effective treatment of clinical conditions associated with ocular surface diseases. In addition, there is a need to address the underlying cause of ocular surface disease.

SUMMARY OF THE INVENTION

Some aspects of the invention provide an ophthalmic formulation consisting essentially of: (a) a pharmaceutically active compound that is capable of reducing the amount of inflammatory neutrophil product on the ocular surface; (b) optionally a second pharmaceutically active compound selected from the group consisting of a steroid, a non-steroidal anti-inflammatory agent (NSAID), a mucolytic agent, and a combination thereof; and (c) a pharmaceutically acceptable ophthalmic excipient.

In some embodiments, the second pharmaceutically active compound comprises methylprednisone, prednisone, dexamethasone, cyclosporine, Lifitegrast®, a non-steroidal anti-inflammatory drug, N-acetylcysteine, Nacystelyn, N-acetylglucosamine (NAG), Dextran, DNaseI (dornase alpha), gelsolin, thymosinβ4, 14- and 15-member macrolide antibiotics or a combination thereof.

The ophthalmic formulation can be in a solution form (e.g., an aqueous solution, a suspension, emulsion, etc.), a gel or an ointment.

Another aspect of the invention provides an ophthalmic formulation consisting essentially of: (a) a pharmaceutically acceptable ophthalmic excipient; (b) a pharmaceutically active compound for treatment of a clinical condition selected from the group consisting of inflammatory and immunological ocular surface disease that can cause symptoms of ocular discomfort, a dry eye syndrome, mucocellular aggregates/debris in tear film, symblepheron formation, fornix foreshortening, eyelid margin/conjunctival keratinization, corneal neovascularization/pannus and subconjunctival fibrosis; and (c) optionally a second pharmaceutically active compound selected from the group consisting of a steroid, an anti-inflammatory agent, a mucolytic agent and a combination thereof. In one particular embodiment, the pharmaceutically active compound comprises heparin.

In another embodiment, the formulation is an eye drop formulation, an ophthalmic gel formulation, a suspension formulation, an emulsion formulation, or an ophthalmic ointment formulation.

Yet in another embodiment, said heparin comprises a coagulant heparin, a non-coagulant heparin, a heparin oligosaccharide or a combination thereof. In some instances, said coagulant heparin comprises unfractionated heparin, a low molecular weight heparin, an ultra-low molecular weight heparin or a combination thereof. Still in other instances, said non-coagulant heparin comprises a sulfation modified heparin, a glycol-split heparin, glycol-split N-acetylated heparin, other heparin derivative, or a combination thereof. In one particular case, said other heparin derivative comprises an N-acetylated heparin or negatively charged nanoparticle mimic of heparin.

In another embodiment, said second pharmaceutically active compound comprises methylprednisone, prednisone, dexamethasone, loteprednol etabonate, fluocinolone, difluprednate, fluorometholone, medrysone, fluocinolone, rimexolone triamcinolone, cyclosporine, Lifitegrast®, tacrolimus, interleukin 1 receptor antagonist (anakinra), other NSAIDs such as ketorolac, diclofenac, flurbiprofen, bromfenac, nepafenac, N-acetylcysteine, N-acetylcysteine, Nacystelyn, Dextran, DNaseI (dornase alpha), gelsolin, thymosinβ4, 14- and 15-member macrolide antibiotics (e.g., erythromycin non-antimicrobial derivative of erythromycin (e.g., EM703 and EM900), clarithromycin, roxithromycin, Fidaxomicin, Telithromycin and azithromycin), or a combination thereof.

Still in another embodiment, the amount of heparin present in said ophthalmic formulation ranges from about 0.01 μg/mL by weight to about 1 g/mL by weight.

Still another aspect of the invention provides a method of using an ophthalmic formulation disclosed herein to treat a clinical condition selected from the group consisting of inflammatory and immunological ocular surface disease that can cause symptoms of ocular discomfort, mucocellular aggregates/debris in tear film, symblepheron formation, fornix foreshortening, eyelid margin/conjunctival keratinization, corneal neovascularization/pannus and subconjunctival fibrosis. In some embodiments, said clinical condition comprises ocular graft-versus-host disease (oGVHD), Steven Johnson syndrome, ocular cicatricial pemphigoid (OCP), mild, moderate and severe tear deficient dry eye disease (DED), meibomian gland disease, superior limbic keratoconjunctivitis (SLK), tear sufficient DED, floppy eyelid syndrome, neurotrophic eye disease, aniridia, keratitis or a postoperative/post-trauma ocular condition. In some instances, said keratitis is due to sterile inflammation or due to a viral, bacterial or fungal infection. Still in other instances, said postoperative/post-trauma ocular condition comprises an ocular condition associated with post-ocular surface reconstruction surgery, antimetabolite application to eye surface, pterygium surgery, glaucoma surgery, keratoprosthesis surgery or radiation injury.

Another aspect of the invention provides an ophthalmic formulation consisting essentially of: (a) a pharmaceutically active compound that is capable of reducing the amount of inflammatory neutrophil product on the ocular surface; (b) optionally a second pharmaceutically active compound selected from the group consisting of a steroid, an anti-inflammatory agent, a mucolytic agent, and a combination thereof; and (c) one or more pharmaceutically acceptable ophthalmic excipients. In some embodiments, said pharmaceutically active compound comprises heparin. Still in other embodiments, the amount of heparin present in said ophthalmic formulation ranges from about 0.01 μg/mL by weight to about 1 g/mL by weight. Yet in another embodiment, said heparin comprises a coagulant heparin, a non-coagulant heparin, a heparin oligosaccharide or a combination thereof. In some instances, said coagulant heparin comprises unfractionated heparin, a low molecular weight heparin, an ultra-low molecular weight heparin or a combination thereof. Still in other instances, said non-coagulant heparin comprises a sulfation modified heparin, a glycol-split heparin, glycol-split N-acetylated heparin, other heparin derivative, or a combination thereof. In one particular case, said other heparin derivative comprises an N-acetylated heparin.

Yet in another embodiment, in the ophthalmic formulation disclosed herein, said second pharmaceutically active compound comprises methylprednisone, prednisone, dexamethasone, loteprednol etabonate, fluocinolone, difluprednate, fluorometholone, medrysone, fluocinolone, rimexolone triamcinolone, cyclosporine, Lifitegrast®, tacrolimus, interleukin 1 receptor antagonist (anakinra), other NSAIDs such as ketorolac, diclofenac, flurbiprofen, bromfenac, nepafenac, N-acetylcysteine, N-acetylcysteine, Nacystelyn, Dextran, DNaseI (dornase alpha), gelsolin, thymosinβ4, 14- and 15-member macrolide antibiotics (e.g., erythromycin, clarithromycin, roxithromycin, Fidaxomicin, Telithromycin and azithromycin), or a combination thereof.

Still in another embodiment, in the ophthalmic formulation disclosed herein, said pharmaceutically acceptable excipient comprises polyvinyl alcohol, povidone, hydroxypropyl methyl cellulose, poloxamers, polyols, Carbopol, pluronics, carbomers, carboxymethyl cellulose, hydroxyethyl cellulose, cyclodextrins, phosphate buffer, citrate buffer, Tris buffer, sodium chloride, potassium chloride, polysorbate 80, vegetable oil, preservative or a combination thereof.

In another embodiment, the ophthalmic formulation comprises multi-dose vials with preservative or a single dose sterile container without preservative.

Still another aspect of the invention provides an ophthalmic formulation comprising a sub-anticoagulant amount of heparin and one or more of a second pharmaceutically active compound comprising an inhibitor of oncostatin M, an inhibitor of LIGHT, an inhibitor of NGAL, DNase I, or a combination thereof. In some embodiments, said inhibitor of oncostatin M comprises a neutralizing antibody of oncostatin M. In other embodiments, said inhibitor of LIGHT comprises a neutralizing antibody of LIGHT. Still in other embodiments, said inhibitor of NGAL comprises a neutralizing antibody of NGAL. Yet in other embodiments, heparin comprises a coagulant heparin, a non-coagulant heparin, a heparin oligosaccharide, or a combination thereof. In some instances, said coagulant heparin comprises unfractionated heparin, a low molecular weight heparin, an ultra-low molecular weight heparin or a combination thereof. In other instances, said non-coagulant heparin comprises a sulfation modified heparin, a glycol-split heparin, glycol-split N-acetylated heparin, other heparin derivative, or a combination thereof. In one particular case, said other heparin derivative comprises an N-acetylated heparin. Still in another embodiment, the amount of heparin is about 500 IU/mL or less. Yet in another embodiment, the amount of heparin is about 300 IU/mL or less. Still yet in another embodiment, the amount of heparin is about 100 IU/mL or less.

Yet another aspect of the invention provides an ophthalmic formulation comprising a sub-anticoagulant amount of heparin. In some embodiments, the amount of heparin is about 1,000 IU/mL or less. Yet in other embodiments, the amount of heparin is about 500 IU/mL or less. Still in other embodiments, the amount of heparin is about 100 IU/mL or less.

Still another aspect of the invention provides a method for treating an ocular disease comprising the steps of administering a therapeutically effective amount of a sub-anticoagulant amount of heparin ophthalmic formulation to a subject in need of such a treatment. In some embodiments, said heparin ophthalmic formulation is administered at least twice a day to said subject. In other embodiments, said heparin ophthalmic formulation is administered at least three times a day to said subject.

Yet still another aspect of the invention provides a method of diagnosing or monitoring an ocular surface disorder in a subject, said method comprising comparing the level of a biomarker from a sample obtained from a subject with the control level of said biomarker to diagnosis or monitor ocular surface disorder in the subject. In some embodiments, said biomarker comprises a plurality of biomarkers. Still in other embodiments, said biomarker comprises Interlukin-8 (IL-8), Oncostatin-M (OSM), Neutrophil gelatinase-associated lipocalin (NGAL), tumor necrosis factor superfamily member 14 (TNFSF14 or LIGHT), or a combination thereof. In some embodiments, said level of biomarker is detected by a method selected from the group consisting of an enzymatic method, a spectrometric method, a chromatographic method, an immunological method, or a combination thereof. In some instances, said step of monitoring comprises determining efficacy of a therapy in a subject having, suspected of having, or of being predisposed to, an ocular surface disorder. Still in other instances, bsaid control level of biomarker comprises the level of said biomarker in the subject prior to commencement of a therapy, the level of said biomarker in the subject at an earlier stage of a therapy, or a combination thereof.

Yet another aspect of the invention provides a diagnostic kit comprising an array of biomarker panels for detecting a biomarker selected from the group consisting of Interlukin-8 (IL-8), Oncostatin-M (OSM), Neutrophil gelatinase-associated lipocalin (NGAL), tumor necrosis factor superfamily member 14 (TNFSF14 or LIGHT), and a combination thereof.

Another aspect of the invention provides identifying underlying cause of at least some of the ocular surface disease. This allows a more effective treatment and methods for identifying appropriate treatment protocol. One particular aspect of the invention provides a method for comparing the level of one or more biomarkers from a sample obtained from the subject with the control. In this manner, the method can be used for diagnosis the ocular surface disease or monitoring the efficacy of a particular treatment. Exemplary biomarkers that can be used in methods of the invention include, but are not limited to, Interlukin-8 (IL-8), Oncostatin-M (OSM), Neutrophil gelatinase-associated lipocalin (NGAL), LIGHT, also known as tumor necrosis factor superfamily member 14 (TNFSF14), and a combination thereof.

BRIEF DESCRIPTION FO THE DRAWINGS

DETAILED DESCRIPTION OF THE INVENTION

Figure 1:
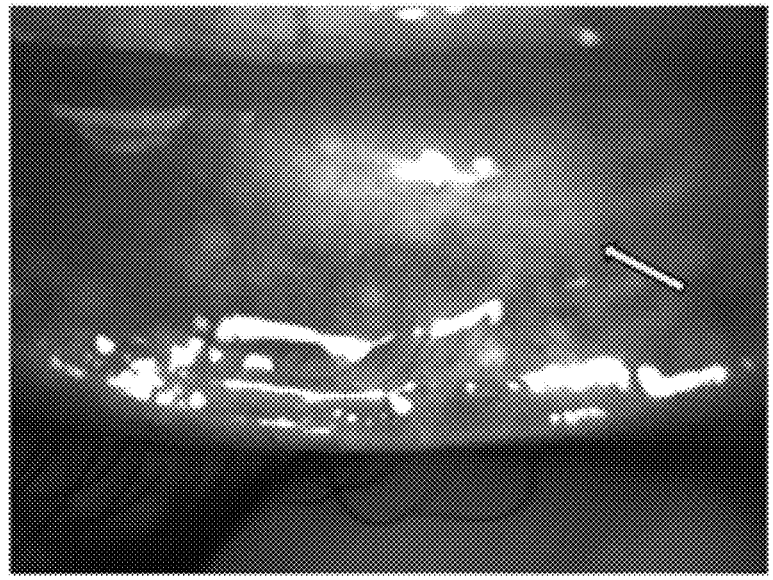
FIG. 1 is a photograph of a patient with tear deficient dry eye and ocular GVHD showing subconjunctival fibrosis caused by an inflammatory and immunological ocular surface disease.

As used in this specification and the appended claims, the singular forms "a," "an" and "the" include plural references unless the content clearly dictates otherwise.

One aspect of the invention provides an ophthalmic formulation consisting essentially of: (a) a pharmaceutically active compound that is capable of reducing the amount of inflammatory neutrophil product on the ocular surface; (b) optionally a second pharmaceutically active compound selected from the group consisting of a steroid, a non-steroidal anti-inflammatory agent (NSAID), a mucolytic agent, and a combination thereof; and (c) a pharmaceutically acceptable ophthalmic excipient. Unless the context requires otherwise, the term "pharmaceutically active compound" refers to a compound that is pharmaceutically active when applied topically to ocular surface. Thus, for example, the term a pharmaceutically active NSAID refers to an NSAID that is pharmaceutically active when applied topically to ocular surface.

Another aspect of the invention provides an ophthalmic formulation consisting essentially of: (a) a pharmaceutically acceptable ophthalmic excipient; (b) a therapeutically effective amount of a pharmaceutically active compound comprising heparin; and (c) optionally a second pharmaceutically active compound selected from the group consisting of a steroid, an anti-inflammatory agent, a mucolytic agent and a combination thereof. The pharmaceutically active compound comprising heparin is capable of treating a clinical condition selected from the group consisting of inflammatory and immunological ocular surface disease that can cause symptoms of ocular discomfort, mucocellular aggregates/debris in tear film, symblepheron formation, fornix foreshortening, eyelid margin/conjunctival keratinization, corneal neovascularization/pannus and subconjunctival fibrosis. "A therapeutically effective amount" means the amount of a compound that, when administered to a mammal for treating a disease or a clinical condition, is sufficient to effect such treatment for the disease. The "therapeutically effective amount" will vary depending on the compound, the disease or the clinical condition and its severity and the age, weight, etc., of the mammal to be treated. "Treating" or "treatment" of a clinical condition or disease includes: (1) preventing the clinical condition or disease, i.e., causing the clinical symptoms of the condition or disease not to develop in a mammal that may susceptible to the clinical condition or disease but does not yet experience or display symptoms of the clinical condition or disease; (2) inhibiting the clinical condition or disease, i.e., arresting or reducing the development of the clinical condition or disease or its symptoms; or (3) relieving the clinical condition or disease, i.e., causing regression of the clinical condition or disease or its symptoms.

Ophthalmic formulations of the invention are useful for treatment of various clinical condition associated with inflammatory and immunological ocular surface diseases. Exemplary clinical conditions that can be treated by ophthalmic formulations of the invention include, but are not limited to, symptoms of ocular discomfort, mucocellular aggregates/debris in tear film, symblepheron formation, fornix foreshortening, eyelid margin/conjunctival keratinization, corneal neovascularization/pannus and subconjunctival fibrosis. More particular examples of clinical conditions that can be treated using ophthalmic formulations of the invention include, but are not limited to, ocular graft-versus-host disease (oGVHD), Steven Johnson syndrome, ocular cicatricial pemphigoid (OCP), mild, moderate and severe tear deficient dry eye disease (DED), meibomian gland disease, superior limbic keratoconjunctivitis (SLK), tear sufficient DED, floppy eyelid syndrome, neurotrophic eye disease, aniridia, keratitis or a postoperative/post-trauma ocular condition, and keratitis due to sterile inflammation or due to a viral, bacterial or fungal infection. Exemplary postoperative/post-trauma ocular conditions that can be treated using ophthalmic formulations of the invention include, but are not limited to, an ocular condition associated with post-ocular surface reconstruction surgery, antimetabolite application to eye surface, pterygium surgery, glaucoma surgery, keratoprosthesis surgery and radiation injury.

Other ocular clinical conditions that can be treated using ophthalmic formulations of the invention include, but are not limited to, dry eye syndrome (keratoconjunctivitis sicca), sjogren's syndrome, congenital alacrima, xerophthalmia (dry eye from vitamin A deficiency), keratomalacia, thyroid eye disease, ocular rosacea, eyelid disorders, meibomian gland disease, meibomian gland dysfunction, ectropion, blepharitis, blepharochalasis, sarcoidosis, stye, hordeolum, chalazion, ptosis, pterygium, eyelid edema, eyelid dermatitis, trichiasis, madarosis, dacryoadenitis, stevens-johnson syndrome, ocular graft versus host disease, dacryocystitis, conjunctivitis, keratoconjunctivitis, blepharoconjunctivitis, blepharokeratoconjunctivitis, allergic conjunctivitis, vernal conjunctivitis, conjunctival suffusion, conjunctivochalasis, subconjunctival hemorrhage, pterygium, pinguecula, chemosis, iritis, iridocyclitis, anterior uveitis, glaucoma, red eye, keratitis, scleritis, episcleritis, peripheral ulcerative keratitis, neurotrophic keratitis, neurotrophic eye disease, corneal ulcer, ulcerative keratitis, corneal abrasion, photokeratitis, ultraviolet keratitis, exposure keratitis, superficial punctuate keratitis, thygeson's superficial punctuate keratopathy, herpes zoster keratitis, acne rosacea, corneal neovascularization, post-operative inflammation following ocular surgery (i.e. eyelid surgery, cataract surgery, corneal surgery, refractive surgery including photorefractive keratectomy, glaucoma surgery, lacrimal gland surgery, conjunctival surgery, eye muscle surgery), ocular surface conditions caused by chemical burns, thermal burns or physical trauma, ocular conditions caused by the following autoimmune or vascular disorders: rheumatoid arthritis, juvenile rheumatoid arthritis, ankulosing spondylitis, reiter's syndrome, enteropathic arthritis, psoriatic arthritis, discoid and systemic lupus erythematosus, multiple sclerosis, graves' disease, antiphospholipid syndrome, sarcoidosis, wegner's granulomatosis, behcet's syndrome, polyarteritis *nodosa*, takayasu's arteritis, dermatomyositis, psoriasis, relapsing polychondritis, vasculitis, sickle cell-anemia, type II diabetes, and diabetic retinopathy.

In some embodiments, ophthalmic formulations of the invention are used to treat a dry eye syndrome. There are two major classes of dry eye syndrome: (i) aqueous tear-deficient dry eye (ADDE) and (ii) evaporative dry eye (EDE). There are also cases of mixed mechanism dry eye (i.e., both ADDE and EDE). ADDE is primarily due to failure of lacrimal tear secretion. ADDE can be further subdivided into Sjogren syndrome dry eye (where the lacrimal and salivary glands are targeted by an autoimmune process, e.g., rheumatoid arthritis) and non-Sjogren's syndrome dry eye (lacrimal dysfunction, but the systemic autoimmune features of Sjogren's syndrome are excluded, e.g., age-related dry eye). In contrast, EDE is primarily due to excessive water loss from the exposed ocular surface in the presence of normal lacrimal secretory function. Its causes can be extrinsic (e.g., ocular surface disorder due to some extrinsic exposure, contact lens wear or vitamin A deficiency) or intrinsic (e.g., Meibomian gland dysfunction and disorders of eyelid aperture). Meibomian glands secrete a mixture of lipids and other components that form the outer layer of the preocular tear film. This lipid layer functions to decrease tear film evaporation. Meibomian gland dysfunction (MGD) leads to evaporative dry eye disease. One of the most well recognized clinic finding in MGD is the presence of numerous telangiectatic blood vessels coursing across the eyelid margin. MGD can also accompany tear deficient dry eye disease, as seen in ocular graft-versus-host-disease (oGVHD). Other specific dry eye syndromes that can be treated using compositions of the invention include keratoconjunctivitis, dry eye caused by conjunctivitis, dry eye caused by allergic conjunctivitis, dry eye caused by blepharitis, dry eye caused by keratitis, dry eye caused by dacryoadenitis, dry eye caused by ocular rosacea, dry eye caused by boehm syndrome, dry eye caused by conjunctivochalasis, dry eye caused by blepharoconjunctivitis, dry eye caused by blepharokeratoconjunctivitis, dry eye caused by superficial punctuate keratitis, dry eye caused by thygeson's superficial punctuate keratopathy, dry eye caused by oGVHD, Sjogren's dry eye syndrome, dry eye caused by Stevens-Johnson syndrome, MGD, dry eye caused by meibomian gland disease, vitamin A deficiency induced dry eye, pharmacological induced dry eye (i.e. hormone replacement therapy, blood pressure medication, antihistamine, antidepressants, anticholinergic medications, glaucoma medication, antihypertensives, diuretics, sedatives, isotretinoin, nasal decongestants, oral contraceptives, beta-blockers, phenothiazines, atropine, pain relieving opiates), pregnancy induced dry eye, LASIK surgery or refractive surgery induced dry eye, dry eye induced by collagen vascular diseases (i.e. systemic lupus erythematosus, Wegener's granulomatosis, rheumatoid arthritis, relapsing polychondritis), dry eye caused by the infiltration of the lacrimal glands by tumors or sarcoidosis, dry eye caused by postradiation fibrosis of tear producing glands, dry eye caused by lacrimal gland, meibomian gland, or goblet cell ablation, dry eye caused by sensory denervation, dry eye caused by thermal or chemical burns, dry eye caused by underlying diabetic conditions, dry eye caused by viral, fungal, or bacterial infection, dry eye caused by prolonged contact lens use, dry eye caused by eyelid disorders or injury to the eyelid (i.e. bulging eyes, drooping eyelid), dry eye caused by corneal dystrophy, dry eye caused by autoimmune disorders, age-induced dry eye, and a combination thereof.

In some particular embodiments, ophthalmic formulations of the invention are used to treat Meibomian gland dysfunction (MGD). Yet in other embodiments, ophthalmic formulations of the invention are used to treat aqueous tear-deficient dry eye (ADDE). In some instances, methods for treating ADDE comprise treating a patient in need of a treatment for Sjogren dry eye syndrome, ocular Graft-Versus-Host-Disease (oGVHD) or non-Sjogren dry eye syndrome. Yet in other embodiments, methods for treating dry eye syndrome comprise treating a patient in need of a treatment of evaporative dry eye (EDE). Still in other embodiments, methods of the invention include treating a patient in need of a treatment for mixed mechanism dry eye consisting of ADDE and EDE. Yet still in other embodiments, methods of the invention include treating a patient suffering from dry eye syndrome due to a complication of refractive eye surgery or is attributable to one or more of the following causes: vitamin A deficiency, ocular surface disorders, allergy, aging, contact lens usage, medication usage or eyelid disorders.

In some embodiments, the ophthalmic formulation consists essentially of heparin as a pharmaceutically active ingredient. Type of heparin that can be used in ophthalmic formulations of the invention include, but are not limited to, (i) coagulation heparin (i.e., heparins having an anticoagulation property) including unfractionated heparin (UFH), low molecular weight heparin (LMWH, e.g., enoxaparin and parnaparin), ultra-low molecular weight heparin (ULMWH) and other heparin species known to one skilled in the art to have anticoagulant property; (ii) non-coagulant heparin (i.e., heparins having no significant anticoagulation property) including, but not limited to, sulfation modified heparin (e.g. 2-0, 3-0 or 6-0 desulfated heparin—ODSH or ODH), Glycol-Split heparins (i.e., gs-heparins), glycol-split N-acetylated heparins, and other heparin species known to one skilled in the art to have no significant anti-coagulation property (e.g., N-Acetylated heparins); (iii) heparin oligosaccharides; and (iv) negatively charged nanoparticles that mimic heparin. Other useful heparin species can be produced by depolymerization using chemical (Deaminative, Oxidative, Alkaline or other), enzymatic or other methods to yield products such as nadroparin, dalteparin, reviparin, parnaparin, ardeparin, bemiparin, enoxaparin, tinzaparin or others.

As used herein, the term "having anti-coagulation property" refers to heparin having at least about 1,000, typically at least about 500, often at least about 300, and more often at least about 200 IU/mL anticoagulant activity. The anticoagulant activity of heparin arises primarily from its ability to bind to antithrombin III (AT III). Thus, the anti-coagulation activity of heparin can be determined by passage of heparin through an immobilized AT III column, also known as an APTT clotting assay. Such a method of measuring anti-coagulation activity is well known to one skilled in the art. See, for example, Barrowcliffe T. W. et al. in "The anticoagulant activity of heparin: measurement and relationship to chemical structure," *J Pharm Biomed Anal.* 1989, 7(2), pp. 217-26, and references cited therein, all of which are incorporated herein by reference in their entirety. The term "having no significant anticoagulation property" refers to heparin having less than about 200 IU/mL, typically less than about 150 IU/mL, often less than about 100 IU/mL, more often less than about 50 IU/mL, and most often less than about 10 IU/mL of anticoagulant activity. Heparin can be a salt form of heparin (e.g., sodium, lithium or potassium salt). In some embodiment, the activity of heparin in the formulation has less than 200 IU/mL, typically about 100 IU/mL or less.

The amount of heparin present in the ophthalmic formulation of the invention can range from about 0.01 µg/mL to about 1 g/mL, typically from about 0.05 µg/mL to about 0.5 g/mL and often from about 1 µg/mL to about 0.1 g/mL by weight.

"Pharmaceutically acceptable excipient" or "pharmaceutically acceptable ophthalmic excipient" means an excipient that is useful in preparing a pharmaceutical composition of the invention. Such an excipient is considered by one skilled in the art as being generally safe, non-toxic and neither biologically active nor otherwise undesirable, and includes excipient that is acceptable for veterinary use as well as human pharmaceutical use. A "pharmaceutically acceptable excipient" as used in the specification and claims includes both one and more than one such excipients. Exemplary pharmaceutically acceptable excipients include a salt (such as sodium chloride) or a tonicity agent, gum, resin, a solvent such as water, a non-aqueous solvents (such as an alcohol, an oil, a buffer solution to maintain pH, a pH modifying agent (e.g., a base such as sodium hydroxide, and an acid such as hydrochloric acid), an emulsifier, a thickening agent, a micro or a nano emulsion forming agent, a preservative, a surfactant, etc. Exemplary pharmaceutically acceptable excipients that can be used in ophthalmic formulations of the invention include, but are not limited to, water, benzyl alcohol, sodium hydroxide, hydrochloric acid, Castrol oil, citrate buffer, Tris buffer, phosphate buffer, as well as other excipients known to one skilled in the art.

In some embodiments, ophthalmic formulations of the invention can also include salts such as sodium chloride. Yet in other embodiments, the ophthalmic formulation of the invention can also include a non-aqueous solvent such as benzyl alcohol, ethanol, or other non-aqueous solvents known to one skilled in the art.

Still in other embodiments, pH of the ophthalmic formulations of the invention is adjusted from pH of about 5.0 to pH of about 8.5, typically from pH of about 5.0 to pH of about 8.0, and often from pH of about 5.0 to pH of about 7.5. The pH of ophthalmic formulations of the invention can be adjusted using, for example, sodium hydroxide and/or hydrochloric acid as needed to achieve a desired pH level.

The ophthalmic formulation can be formulated as an eyedrop, an ointment, or a gel (e.g., heparin sodium in hydrogel). The ophthalmic formulation can also be formulated as a nanoemulsion of oil or a suspension In some embodiments, ophthalmic formulations of the invention are preservative free and are formulated for a single-use or in a multi-dose vials. If a preservative is used, suitable preservatives include, but are not limited to, benzalkonium, purite, chlorobutanol, sodium perborate, stabilized oxychloro complex (SOC), Polyquaternium-1 (Polyquad, PQ-1), Thimerosal, Benzyl alcohol, Sorbic acid, Methyl/propyl paraben, Chlorhexidine, Disodium EDTA, sofZia, and other preservatives known to one skilled in the art of ophthalmology or ophthalmic formulation chemistry.

When present, the second pharmaceutically active compound is selected from the group consisting of a steroid, an anti-inflammatory agent, a mucolytic agent and a combination thereof. Exemplary steroids that are suitable in ophthalmic formulations of the invention include, but are not limited to, methylprednisone, prednisone, dexamethasone, loteprednol etabonate, fluocinolone, difluprednate, fluorometholone, medrysone, fluocinolone, rimexolone triamcinolone, and a combination thereof. When a steroid is used in ophthalmic formulations of the invention, the amount of steroid present in the formulation ranges from about 0.01% w/w to 2% w/w; typically from about 0.05% w/w to 1% w/w, and often from about 0.1% w/w to about 0.3% w/w. It should be appreciated that the scope of the invention is not limited to these particular ranges of the amount of steroid. In particular, the amount of steroid present in ophthalmic formulations of the invention generally depends on the steroid used. For example, the amount of steroid present can vary depending on the activity of the particular steroid used, molecular weight of the steroid, as well as the purpose of using a steroid in ophthalmic formulations of the invention.

Exemplary anti-inflammatory agents that are suitable in ophthalmic formulations of the invention include, but are not limited to, cyclosporine, Lifitegrast®, tacrolimus, interleukin 1 receptor antagonist (anakinra), other NSAIDs such as ketorolac, diclofenac, flurbiprofen, bromfenac, nepafenac, and a combination thereof. When an anti-inflammatory agent is used in ophthalmic formulations of the invention, the amount of anti-inflammatory agent present in the formulation ranges from about 0.01% w/w to 2% w/w; typically from about 0.05% w/w to 1% w/w, and often from about 0.1% w/w to about 0.3% w/w. It should be appreciated that the scope of the invention is not limited to these particular ranges of the amount of anti-inflammatory agent. In particular, the amount of anti-inflammatory agent present in ophthalmic formulations of the invention generally depends on the particular anti-inflammatory agent used, such as the activity of the particular anti-inflammatory agent used, molecular weight of the anti-inflammatory agent, etc.

Exemplary mucolytic agents that are useful in ophthalmic formulations of the invention include, but are not limited to, N-acetylcysteine, Nacystelyn, Dextran, DNaseI (dornase alpha), gelsolin, thymosinβ4, 14- and 15-member macrolide antibiotics (e.g., erythromycin, a non-antimicrobial derivative of erythromycin (e.g., EM703 and EM900), clarithromycin, roxithromycin, Fidaxomicin, Telithromycin and azithromycin), and a combination thereof. It should be appreciated that when an antibiotic is used, it is primarily used for its mucolytic activity. When a mucolytic agent is used in ophthalmic formulations of the invention, the amount of mucolytic agent present in the formulation ranges from about 0.01% w/w to 2% w/w; typically from about 0.05% w/w to 1% w/w, and often from about 0.1% w/w to about 0.3% w/w. It should be appreciated that the scope of the invention is not limited to these particular ranges of the amount of mucolytic agent. In particular, the amount of mucolytic agent present in ophthalmic formulations of the invention generally depends on the particular mucolytic agent used, such as the activity of the mucolytic agent, molecular weight of the mucolytic agent, etc.

Ophthalmic formulations of the invention can be homogeneous or heterogeneous. In some embodiments, ophthalmic formulations of the invention contain an oil or a fatty acid ester. A fatty acid ester has the meaning commonly understood in the art, being an ester formed between an alcohol and a fatty acid. Exemplary fatty acid esters that are useful in formulations of the invention include, but are not limited to, triglyceride esters commonly known as vegetable oils, mono and diglyceride esters of fatty acids, fatty acid methyl esters, as well as other fatty acid esters that are known to one skilled in the art. It should be appreciated the fatty acid ester can be a mixture of several chemical compounds or an essentially pure compound. Typically, the fatty acid ester is a vegetable oil. Particular examples of vegetable oils that can be used include, but are not limited to, castor oil, sesame oil, soybean oil, cottonseed oil, olive oil, peanut oil, safflower oil, sunflower oil, palm oil, palm kernel oil, canola oil, and Miglyol Oil®.

Various vehicles can be used in the ophthalmic formulations of the invention. These vehicles include, but are not limited to, purified water (water), polyvinyl alcohol, povidone, hydroxypropyl methyl cellulose, poloxamers, carboxymethyl cellulose, hydroxyethyl cellulose, polyols, sodium hyaluronate, pluronics, corbopol, cyclodextrin and a mixture of two or more thereof. The vehicle is used in the formulation in amounts as needed to provide the concentration of the active compound(s) disclosed herein. In one particular embodiment, the vehicle comprises water.

In some embodiments of this invention, an emulsion stabilizing polymer is used. While not intending to limit the scope of the invention, emulsion stabilizing polymers generally contain hydrophilic groups such as cellulose, sugars, ethylene oxide, hydroxide, carboxylic acids or other polyelectrolytes. Without being bound by any theory, it is believed that these polymers help to stabilize emulsions by increasing the viscosity of the formulation as well as by reducing the interfacial tension. Surfactants such as polysorbate 80 or other surfactants acceptable for Opthalmics can be used to stabilize emulsions, Some examples of emulsion stabilizing polymers useful in this invention include, but are not limited to, carbomers, Pemulen®, sodium carboxymethylcellulose, hydroxypropylmethylcellulose, povidone, polyvinyl alcohol, polyethylene glycol and a mixture of two or more thereof.

The ophthalmic formulations of the present invention can be packaged in various package forms known in the field of topical ophthalmic. In one particular embodiment, the ophthalmic formulation is packaged in sterile, preservative-free single-use packs or vials or containers (i.e., the unit dose vials). Each vial, for example as small as a 0.9 mL, may be made of low density polyethylene so as to contain a small quantity of the formulation, e.g., 0.4 mL for a single use. This way, where the ophthalmic formulation is sterilized and contained in disposable single-dose containers for topical use in drop form, multiple vials in the form of a set of 30 vials, 60 vials and so on can be packaged in a tray with a lid, for example, a polypropylene tray with an aluminum peelable lid. The entire contents of each tray can be dispensed intact, and one vial or pack is used each time and immediately discarded after each use. For example, plastic ampules or vials or containers can be manufactured using blow-fill-seal (BFS) technology. The BFS processes may involve plastic extrusion, molding, aseptic filling, and hermetic sealing in one sequential operation and those processes are known in the art. In another embodiment, the formulation is packaged in multi-dose vials such that the materials can be dispensed as sterile at each time using specialized container/closure maintaining the sterility integrity. In yet another embodiment, the ophthalmic formulation is packaged in conventional vials/containers as a sterile product.

In some embodiments, the dosage form of the invention is eye drops of heterogeneous aqueous solution, eye drop formulations.

In one particular embodiment, ophthalmic formulation comprising heparin is formulated as eye drops and are used to treat inflammatory and immunological ocular surface disease that can cause symptoms of ocular discomfort, mucocellular aggregates/debris in tear film, symblepheron formation, fornix foreshortening, eyelid margin/conjunctival keratinization, corneal neovascularization/pannus or subconjunctival fibrosis. Specific clinical conditions that can be treated using ophthalmic formulations of the invention include such diseases as ocular graft-versus-host disease (oGVHD), Steven Johnson syndrome, ocular cicatricial pemphigoid (OCP), mild, moderate and severe tear deficient dry eye disease (DED) (secondary to sjogrens syndrome, non-sjogrens syndrome, idiopathic and other causes), meibomian gland disease (dysfunction or atrophy), superior limbic keratoconjunctivitis (SLK), tear sufficient DED (concordant or discordant), floppy eyelid syndrome, neurotrophic eye disease, aniridia and postoperative/post-trauma pathologies, e.g., after ocular surface reconstruction surgery, antimetabolite application to eye surface (mitomycin-C, 5-fluorouracil and others) or keratoprosthesis surgery or radiation injury.

In some embodiments, ophthalmic formulations of the invention comprising heparin are used for its anti-inflammatory action especially its action of neutralizing inflammatory products of neutrophils. Without being bound by any theory, it is believed that in some instances, heparanase inhibition over the ocular surface and within eye tissues also contributes to heparin therapeutic effect for clinical beneficial effects in DED. As shown in the Examples section below, the present inventors have discovered that neutrophil products are pro-inflammatory and pro-fibrotic; therefore, heparin activity is believed to be beneficial in reducing inflammatory mucocellular aggregates in tear film and reducing fibrous complications such as symblepheron and conjunctival fornix foreshortening.

Another aspect of the invention provides an ophthalmic formulation comprising a sub-anticoagulant amount of heparin and one or more of a second pharmaceutically active compound. Typically, the second pharmaceutically active compound includes an inhibitor of oncostatin M, an inhibitor of LIGHT, an inhibitor of NGAL, DNase I, an inhibitor of IL-8 or a combination thereof. The term "sub-anticoagulant amount" when referring to the amount of heparin, it mean about 1,000 IU/mL or less, typically about 500 IU/mL or less, often about 300 IU/mL or less and more often about 100 IU/mL or less. Alternatively, the term "sub-anticoagulant amount" means less than the Food and Drug Administration ("FDA") approved or recommended dosage for therapeutic use in achieving anticoagulation, typically at least about 90% or less, often at least about 75% or less, more often about 50% or less of FDA approved or recommended anticoagulant dosage.

In some embodiments, an inhibitor of oncostatin M, an inhibitor of LIGHT, or NGAL comprises a corresponding neutralizing antibody. The neutralizing antibody can be a selective binder to the corresponding protein. NGAL refers to neutrophil gelatinase-associated lipocalin. LIGHT (i.e., a protein that is "homologous to Lymphotoxin, exhibits Inducible expression and competes with HSV Glycoprotein D for binding to Herpes virus entry mediator, a receptor expressed on T lymphocytes") refers to protein that is secreted by a tumor necrosis factor superfamily, in particular by tumor necrosis factor superfamily member 14 (TNFSF14).

The phrase "selective binder" means the ability of an antibody, antigen binding fragment or binding partner (antigen binding peptide) to preferentially bind to the corresponding protein. Often the phrase "selective binder" refers to a moiety that specifically binds to the corresponding protein (e.g., an antibody, fragment thereof, or binding partner to an antigen), where the level of binding, as measured by any standard assay (e.g., an immunoassay), is statistically significantly higher than the background control for the assay. For example, when performing an immunoassay, controls typically include a reaction well/tube that contain antibody or antigen binding fragment alone (i.e., in the absence of the protein), wherein an amount of reactivity (e.g., non-specific binding to the well) by the antibody or antigen binding fragment thereof in the absence of the protein is considered to be background. Binding can be measured using a variety of methods standard in the art including enzyme immunoassays (e.g., ELISA), immunoblot assays, etc.).

Inhibitors of a given protein can be purified to varying degrees. Whole antibodies can be polyclonal or monoclonal. Alternatively, functional equivalents of whole antibodies, such as antigen binding fragments in which one or more antibody domains are truncated or absent (e.g., Fv, Fab, Fab', or $F(ab)_2$ fragments), as well as genetically-engineered antibodies or protein binding fragments thereof, including single chain antibodies or antibodies that can bind to more than one epitope (e.g., bi-specific antibodies), or antibodies that can bind to one or more different antigens (e.g., bi- or multi-specific antibodies), can also be employed in the invention.

Generally, in the production of an antibody, a suitable experimental animal, such as, for example, but not limited to, a rabbit, a sheep, a hamster, a guinea pig, a mouse, a rat, or a chicken, is exposed to an antigen, i.e., protein (e.g., oncostatin M, LIGHT protein, IL-8, or NGAL) against which an antibody is desired. Typically, an animal is immunized with an effective amount of antigen that is injected into the animal. An effective amount of antigen refers to an amount needed to induce antibody production by the animal. The animal's immune system is then allowed to respond over a pre-determined period of time. The immunization process can be repeated until the immune system is found to be producing antibodies to the antigen. In order to obtain polyclonal antibodies specific for the antigen, serum is collected from the animal that contains the desired antibodies (or in the case of a chicken, antibody can be collected from the eggs). Such serum is useful as a reagent. Polyclonal antibodies can be further purified from the serum (or eggs) by, for example, treating the serum with ammonium sulfate.

Monoclonal antibodies can be produced according to the methodology of Kohler and Milstein (*Nature*, 1975, 256, 495-497). For example, B lymphocytes are recovered from the spleen (or any suitable tissue) of an immunized animal and then fused with myeloma cells to obtain a population of hybridoma cells capable of continual growth in suitable culture medium. Hybridomas producing the desired antibody are selected by testing the ability of the antibody produced by the hybridoma to bind to the desired antigen.

Still in some embodiments, the amount of heparin is about 1,000 IU/mL, typically about 500 IU/mL or less, often about 300 IU/mL or less, and more often about 100 IU/mL or less. The term "about" when referring to a numeric value means±20%, typically ±10%, often ±5% and most often ±2% of the numeric value.

Yet in another aspect of the invention provides an ophthalmic formulation comprising a sub-anticoagulant amount of heparin. In one embodiment, the amount of heparin is about 1,000 IU/mL or less. Still in another embodiment, the amount of heparin is about 500 IU/mL or less. In another embodiment, the amount of heparin is about 100 IU/mL or less.

In yet another aspect of the invention provides a method for treating an ocular disease to a subject in need of such a treatment. Such a method generally involves administering a therapeutically effective amount of a sub-anticoagulant amount of heparin ophthalmic formulation to the subject to treat an ocular disease. In some embodiments, the heparin ophthalmic formulation is administered at least twice a day to said subject. Still in other embodiments, the heparin ophthalmic formulation is administered at least three times a day to said subject. The ophthalmic formulation can be an aqueous solution, aqueous suspension, gel, etc.

Another aspect of the invention provides a method for diagnosing or monitoring an ocular surface disorder in a subject. The method includes comparing the level of a biomarker from a sample obtained from a subject with the control level of said biomarker to diagnosis or monitor ocular surface disorder in the subject. As used herein, the term "control level" of a biomarker refers to the level against which biomarker level in the test sample can be compared including (i) those of a subject not having an ocular surface disorder, (ii) those of a subject having an ocular surface disorder, (iii) level of biomarker from the same subject prior to a treatment, just after starting a treatment, or prior to showing any symptoms of an ocular surface disorder.

In some embodiments, the control level can be a normal level, meaning the level in a sample from a normal patient, i.e., a subject not having an ocular surface disorder. This control level can be referred to more specifically as a "negative control". This allows a determination based on the control level of biomarker, where a sample to be evaluated for an ocular surface disease has a measureable difference or substantially no difference in the biomarker level as compared to the control level.

In another embodiment, the control level can be the level of biomarker established in a sample from the subject or from a population of individuals which is believed to have an ocular surface disease. This can be more specifically referred to as a "positive control level".

The term "positive control" as used herein refers to a level of biomarker expression or biological activity established in a sample from a subject, from another individual, or from a population of individuals, where the sample was believed, based on data from that sample, to have the disease.

In other embodiments, the control level can be established from a previous sample from the subject being tested, so that the disease progression or regression of the subject can be monitored over time and/or the efficacy of treatment can be evaluated.

In one particular embodiment, a panel of four novel biomarkers in the tear fluid sample from a subject was identified that can be used as biomarkers to diagnosis or monitor an ocular surface disease or effectiveness of a treatment thereof. Each biomarker can be individually used or analyzed. Alternatively, two or more biomarkers can be used or analyzed for diagnosis or monitoring. Unless otherwise stated or the context requires otherwise, the term "monitor" refers to determining the progression of an ocular surface disease or determining the effectiveness of a particular treatment protocol or a drug. The term "diagnosis" refers to a process of determining the presence or the absence of an ocular surface disease in a subject. It can also include determining which particular ocular surface disease is present in the subject.

In one particular embodiment, methods of the invention include using one or more of the following biomarkers: (i) Interlukin-8 (IL-8), (ii) Oncostatin-M (OSM), (iii) Neutrophil gelatinase-associated lipocalin (NGAL) and (iv) LIGHT, also known as tumor necrosis factor superfamily member 14 (TNFSF14). In one particular embodiment, the method uses one biomarker. Yet in another embodiment, the method uses two or more biomarkers. Still in another embodiment, the method uses four biomarkers. It has been found by the present inventors that the level of these four biomarker proteins are increased in tear fluid/ocular surface washings of patients with ocular surface diseases as compared to healthy subjects, i.e., subjects who do not have an ocular surface disease.

The present inventors have also discovered that these biomarker proteins are increased in processes that contribute to the pathophysiology of ocular surface diseases. In particular, it was found that IL-8 is increased in ocular surface inflammation which clinically can manifest as Bulbar Redness and mucocellular aggregates. OSM increase is associated with epithelial barrier breakdown which can manifest as Corneal fluorescein staining. LIGHT increase is associated with immunoproliferation and stimulation of adaptive immune responses. NGAL increase is associated with Meibomian gland disease that manifests as evaporative Dry Eye.

The biomarkers can be used for diagnosing ocular surface diseases to initiate appropriate therapy or treatment, e.g., with Heparin eye drops or another appropriate pharmaceutical product. It can also direct the choice of therapeutic agent to initiate treatment, either with Heparin as a single agent or with other active pharmacological agents, either alone or in combination with Heparin. These pharmacological agents may be inhibitors of one or more of the biomarker proteins (i.e., IL-8, OSM, NGAL, and LIGHT). The inhibitors can be peptides, antibodies, aptamers, small molecules etc. The term "aptamer" (sometimes referred to as nucleic acid antibody) is used herein to refer to a single- or double-stranded DNA or a single-stranded RNA molecule that recognizes and binds to a desired target molecule by virtue of its shape. The term "aptamer" can also include peptide molecules that provide specific or selective binding. See e.g., Hoppe-Seyler et al., *J. Ster. Biochem. Mol. Biol.,* 2001, 78, pp. 105-111, which is incorporated herein by reference in its entirety. One skilled in the art can readily produce an aptamer by using the procedures known to one skilled in the art. See, for example, PCT Publication Nos. WO92/14843, WO91/19813, and WO92/05285, the disclosures of which are incorporated by reference herein. Individual biomarker proteins may point to specific therapies. For example, IL-8 increase may point to using anti-inflammatory therapy (e.g., Restasis, Xiidra, Brimonidine, Heparin eye drops or Steroids). OSM increase may point to using non-preserved tears/ointments, Heparin eye drops, Serum Tears or contact lens. LIGHT increase may point to using Heparin, Tacrolimus or steroids/NSAIDS. NGAL increase may point to using Erythromycin ointment, Doxycycline PO or Heparin eye drops.

Changes in the levels of biomarker proteins can be used to assess response to or effectiveness of therapy. The treatment intensity can also be titrated to biomarker levels.

The method can be used for providing a rapid result, in-office test to diagnose and manage cicatrizing ocular surface diseases, and initiate/titrate Heparin eye drop therapy for such diseases, either as a single agent or in combination with other active pharmacological agents.

Methods of the invention utilizing the biomarker can also be used for diagnosing or monitoring ocular surface disorders such as oGVHD or Sjogren's Syndrome and other Dry Eye Disease. Such methods typically include measuring the level of one or more biomarkers present in a biological sample taken from a test subject (e.g., tear fluid, blood/serum, or ocular surface cells) and comparing to a control level. The control level can be prior biomarker level of the subject, biomarker level of healthy subject, or biomarker level of subject(s) with an ocular surface disease.

Another aspect of the invention provides sensors, biosensors, multi-analyte panels, arrays, assays and kits for determining the level of one or more biomarkers obtained from the subject. The biomarkers and methods in which they are employed can be used to assist diagnosis and to assess onset and development of ocular surface disorders. The invention also relates to use of biomarkers in clinical screening, assessment of prognosis, evaluation of therapy, for drug screening and drug development.

In particular aspect, the invention provides a method of diagnosing or monitoring ocular surface disorders in a subject, comprising: obtaining a biological sample from the subject, and comparing the level of one or more biomarkers in the biological sample with the control level.

The level of biomarker(s) can be determined readily using any of the conventional methods available to one skilled in the art. Exemplary methods include, but are not limited to, direct or indirect methods such as coupled or uncoupled enzymatic methods, electrochemical, spectrometric (e.g., spectrophotometric such as using a UV/VIS spectrometer, fluorometric, luminometric, polarimetric, etc.) chromatographic (e.g., HPLC, gas chromatography, MPLC, LPLC, etc.), an immunological method such as ELISA, etc.

Yet another aspect of the invention provides a method of diagnosing or monitoring ocular surface disorders, or predisposition thereto. Such a method includes comparing the level of one or more biomarkers present in a biological sample taken from a test subject and comparing it with the control level. In one particular embodiment, the method of the invention is used to monitor efficacy of a therapy (e.g. a therapeutic substance) in a subject having, suspected of having, or of being predisposed to, an ocular surface disorder.

Still another aspect of the invention provides a multi-analyte panel or array capable of detecting one, two, three or four biomarkers of the invention. The multi-analyte panel is capable of detecting a number of different analytes. An array is capable of detecting a single analyte in a number of samples or, as a multi-analyte array, is capable of detecting a number of different analytes in a sample. A multi-analyte panel or multi-analyte array according to the invention is capable of detecting one or more biomarker as described herein, and is capable of detecting a biomarker or biomarkers additional to those specifically described herein.

Also provided is a diagnostic or monitoring test kit suitable for performing a method according to the invention, optionally together with instructions for use of the kit. The diagnostic or monitoring kit may comprise one or more biosensors according to the invention, a single sensor, or biosensor or combination of sensors and/or biosensors may be included in the kit. A diagnostic or monitoring kit may comprise a panel or an array according to the invention. A diagnostic or monitoring kit may comprise an assay or combination of assays according to the invention.

Further provided is the use of one or more biomarkers selected from (i) Interlukin-8 (IL-8), (ii) Oncostatin-M (OSM), (iii) Neutrophil gelatinase-associated lipocalin (NGAL) and (iv) LIGHT, also known as tumor necrosis factor superfamily member 14 (TNFSF14), to diagnose and/or monitor an ocular surface disorder.

Yet further provided is the use of a method, sensor, biosensor, multi-analyte panel, array or kit according to the invention to identify a substance capable of modulating or treating ocular surface disorders. A substance capable of modulating or treating ocular surface disorders may be an anti-inflammatory, immunomodulatory, immunosuppressive, antibiotic substance or palliative (artificial tears, contact lenses, or punctal plugs) useful for treatment of ocular surface disorders. Throughout this specification and the appended claims, the term "treating" or "treatment" of a disease includes: (1) preventing the disease, i.e., causing the clinical symptoms of the disease not to develop in a subject or predisposed to the disease but does not yet experience or display symptoms of the disease; (2) inhibiting the disease, i.e., arresting or reducing the development of the disease or its clinical symptoms; or (3) relieving the disease, i.e., causing regression of the disease or its clinical symptoms.

A higher level of biomarkers (e.g., IL-8, OSM, LIGHT, NGAL, or a combination of two or more thereof) in the test biological sample relative to the negative control level (e.g., level of biomarker(s) in a subject who has no ocular surface disease) is indicative of the presence of an ocular surface disorder, such as, oGVHD, Sjogren's Syndrome and other Dry Eye Disease.

Methods of monitoring and of diagnosis according to the invention are useful to confirm the existence of an ocular surface disorder, or predisposition thereto; to monitor development of ocular surface disorder by assessing onset and progression, or to assess amelioration or regression of the disorder. Methods of monitoring and of diagnosis are also useful in methods for assessment of clinical screening, prognosis, choice of therapy, evaluation of therapeutic benefit, i.e. for drug screening and drug development. Efficient diagnosis and monitoring methods provide very powerful "patient solutions" with the potential for improved prognosis, by establishing the correct diagnosis, allowing rapid identification of the most appropriate treatment (thus lessening unnecessary exposure to harmful drug side effects), reducing "down-time" and relapse rates.

Methods for monitoring efficacy of a therapy can be used to monitor the therapeutic effectiveness of existing therapies and new therapies in human subjects and in non-human animals (e.g., in animal models). These monitoring methods can be incorporated into screens for new drug substances and combinations of substances. Modulation of a protein biomarker level is useful as an indicator of the state of the ocular surface disorder or predisposition thereto. An increase in the level of protein biomarker over time is indicative of onset or progression, i.e., worsening of the disorder, whereas a decrease in the level of protein biomarker indicates amelioration or remission of the disorder. The identification of biomarkers for ocular surface disorders permits integration of diagnostic procedures and therapeutic regimes. Currently there no methodologies available to determine effective treatment and it has not hitherto been possible to perform rapid assessment of drug response. Traditionally, many ocular surface disease therapies have required treatment trials lasting weeks to months for a given therapeutic approach. Detection of a protein biomarker of the invention can be used to screen subjects prior to their participation in clinical trials. The biomarker provides a means to indicate therapeutic response, failure to respond, unfavorable side-effect profile, degree of medication compliance and achievement of adequate serum drug levels. The biomarker may be used to provide warning of adverse drug response, a major problem encountered with all ocular surface disease medications. Biomarkers are useful in development of personalized ocular surface disease therapies, as assessment of response can be used to fine-tune dosage, minimize the number of prescribed medications, reduce the delay in attaining effective therapy and avoid adverse drug reactions. Thus by monitoring a biomarker of the invention, patient care can be tailored precisely to match the needs determined by the disorder and the pharmacogenomic profile of the patient, the biomarker can thus be used to titrate the optimal dose, predict a positive therapeutic response and identify those patients at high risk of severe side effects.

The term "biomarker" means a distinctive biological or biologically derived indicator of a process, event, or condition. Protein biomarkers can be used in methods of diagnosis, e.g., clinical screening, and prognosis assessment; and in monitoring the results of therapy, for identifying patients most likely to respond to a particular therapeutic treatment, as well as in drug screening and development. Biomarkers and uses thereof are valuable for identification of new drug treatments and for discovery of new targets for drug treatment.

Measurement of biomarker can be performed by a direct or indirect detection method. The biomarkers can be detected directly, or indirectly, via interaction with a ligand or ligands, such as an enzyme, binding receptor or transporter protein, antibody, peptide, aptamer, or oligonucleotide, or any synthetic chemical receptor or compound capable of specifically binding the biomarker. The ligand may possess a detectable label, such as a luminescent, fluorescent or radioactive label and/or an affinity tag.

In one particular embodiment, the biomarkers of the invention are detected and measured using mass spectrometry-based techniques; chromatography-based techniques; enzymatic detection systems (by direct or indirect measurements); or using sensors, e.g. with sensor systems with amperometric, potentiometric, conductimetric, impedance, magnetic, optical, acoustic or thermal transducers. A sensor may incorporate a physical, chemical or biological detection system. An example of a sensor is a biosensor, i.e., a sensor with a biological recognition system, e.g., based on a nucleic acid, such as an oligonucleotide probe or aptamer, or a protein such as an enzyme, binding protein, receptor protein, transporter protein or antibody. The biosensor may incorporate an immunological method for detection of the biomarker, an electrical, thermal, magnetic, optical (e.g., hologram) or acoustic technologies. Using such biosensors, it is possible to detect the target biomarker at the anticipated concentrations found in biological samples. Methods of the invention are suitable for clinical screening, assessment of prognosis, monitoring the results of therapy, identifying patients most likely to respond to a particular therapeutic treatment, for drug screening and development, and to assist in identification of new targets for drug treatment. The identification of key biomarkers specific to a disease is central to integration of diagnostic procedures and therapeutic regimes.

Methods involving detection and/or quantification of the biomarker of the invention can be performed using benchtop instruments, or can be incorporated onto disposable, diagnostic or monitoring platforms that can be used in a non-laboratory environment, e.g. in the physician's office or at the patient's bedside. Suitable sensors or biosensors for performing methods of the invention include "credit" cards with optical or acoustic readers. Sensors or biosensors can be configured to allow the data collected to be electronically transmitted to the physician for interpretation and thus can form the basis for e-medicine.

Additional objects, advantages, and novel features of this invention will become apparent to those skilled in the art upon examination of the following examples thereof, which are not intended to be limiting. In the Examples, procedures that are constructively reduced to practice are described in the present tense, and procedures that have been carried out in the laboratory are set forth in the past tense.

EXAMPLES

Example 1

Inflammatory and immunological ocular surface disease causes subconjunctval fibrosis (i.e., scarring). FIG. 1 is a photo of a patient with tear deficient dry eye and ocular GVHD. Arrow points to area of subconjunctival fibrosis that is caused due to epithelial mesenchymal transition (EMT), a process that is induced by exposure to neutrophil inflammatory products. Heparins reduced the amount of neutrophil inflammatory products and neutrophil inflammatory strands. Therefore, heparins can reduce the EMT and fibrosis to treat tear deficient dry eye and ocular GVHD.

Example 2

Figure 2:
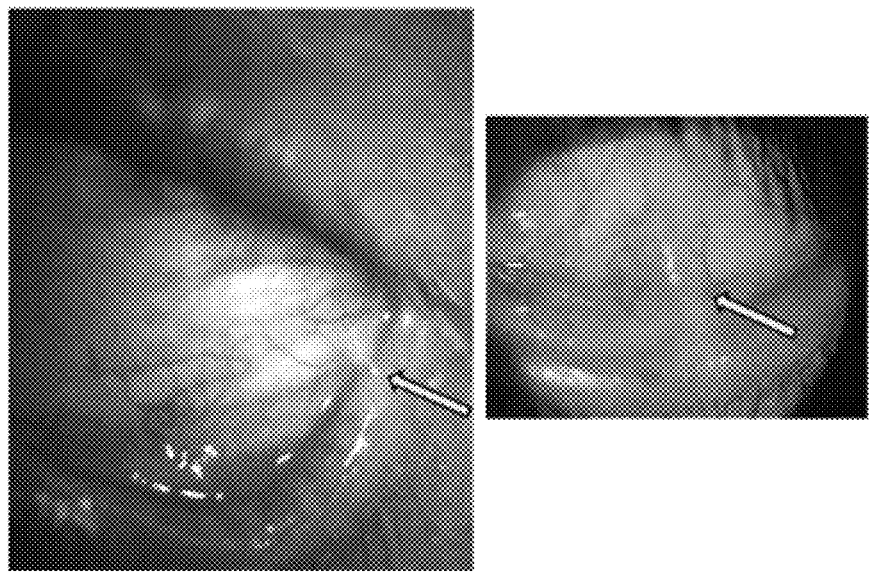
FIG. 2 is a photograph of a patient with tear deficient dry eye and ocular GVHD.

Inflammatory and immunological ocular surface disease causes symblepheron formation. FIG. 2 is a photo of a patient with tear deficient dry eye and ocular GVHD. Arrow points to area of symblepheron that is caused due to epithelial mesenchymal transition (EMT) and alpha smooth muscle actin upregulation, a process that is induced by exposure to neutrophil inflammatory products. Heparins reduced the amount of neutrophil inflammatory products and neutrophil inflammatory strands. Therefore, heparins can be used to treat symblepheron.

Example 3

Figure 3:
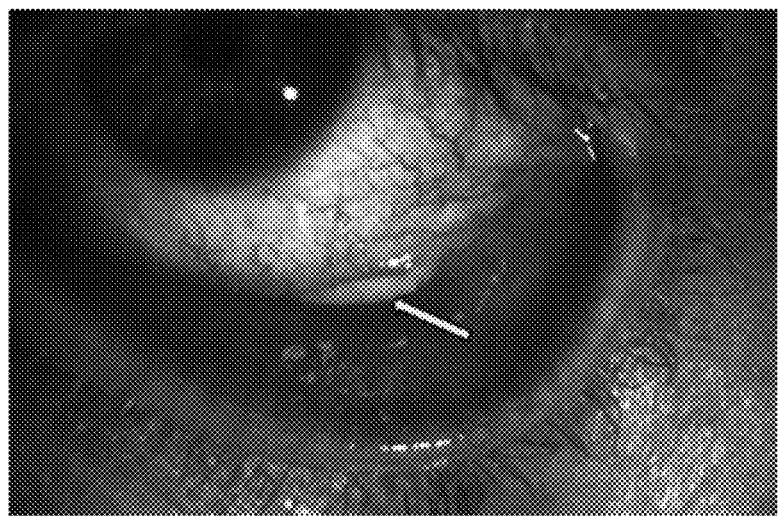
FIG. 3 is a photograph of a patient with tear deficient dry eye.

Inflammatory and immunological ocular surface disease causes mucocellular aggregates. FIG. 3 is a photo of a patient with tear deficient dry eye. Arrow points to mucocellular aggregate. Heparins reduced mucocellular aggregates and neutrophil inflammatory strands. Therefore, heparins can reduce inflammation and fibrosis and are used to prevent or treat symblepheron, subconjunctival fibrosis and fornix foreshortening and dry eye diseases.

Example 4

Figure 4:
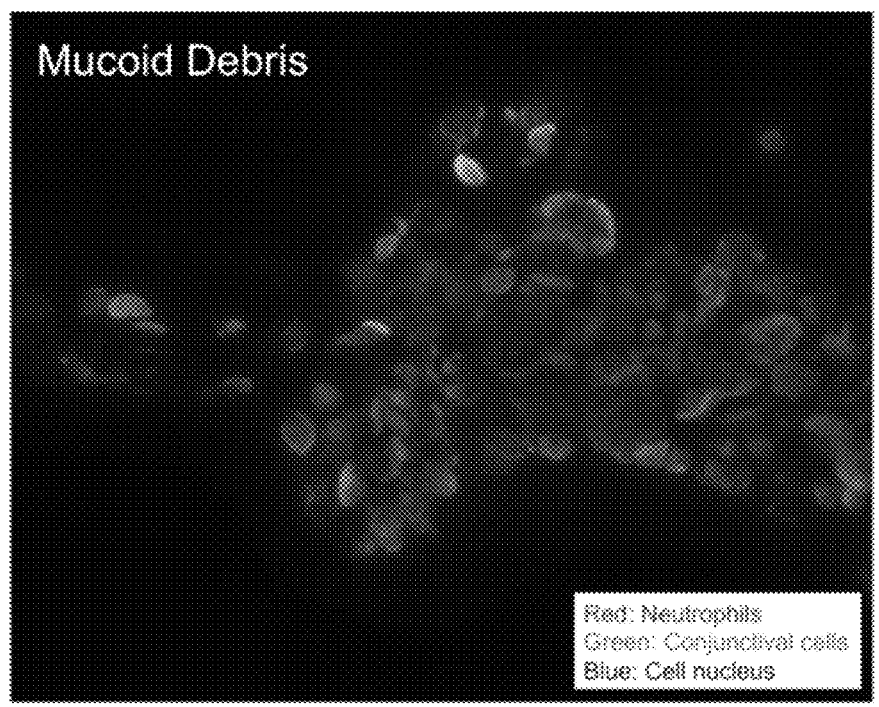
FIG. 4 is a photograph of mucocellular aggregates containing neutrophils (red stained cells) and their inflammatory and profibrotic products.
Figure 5:
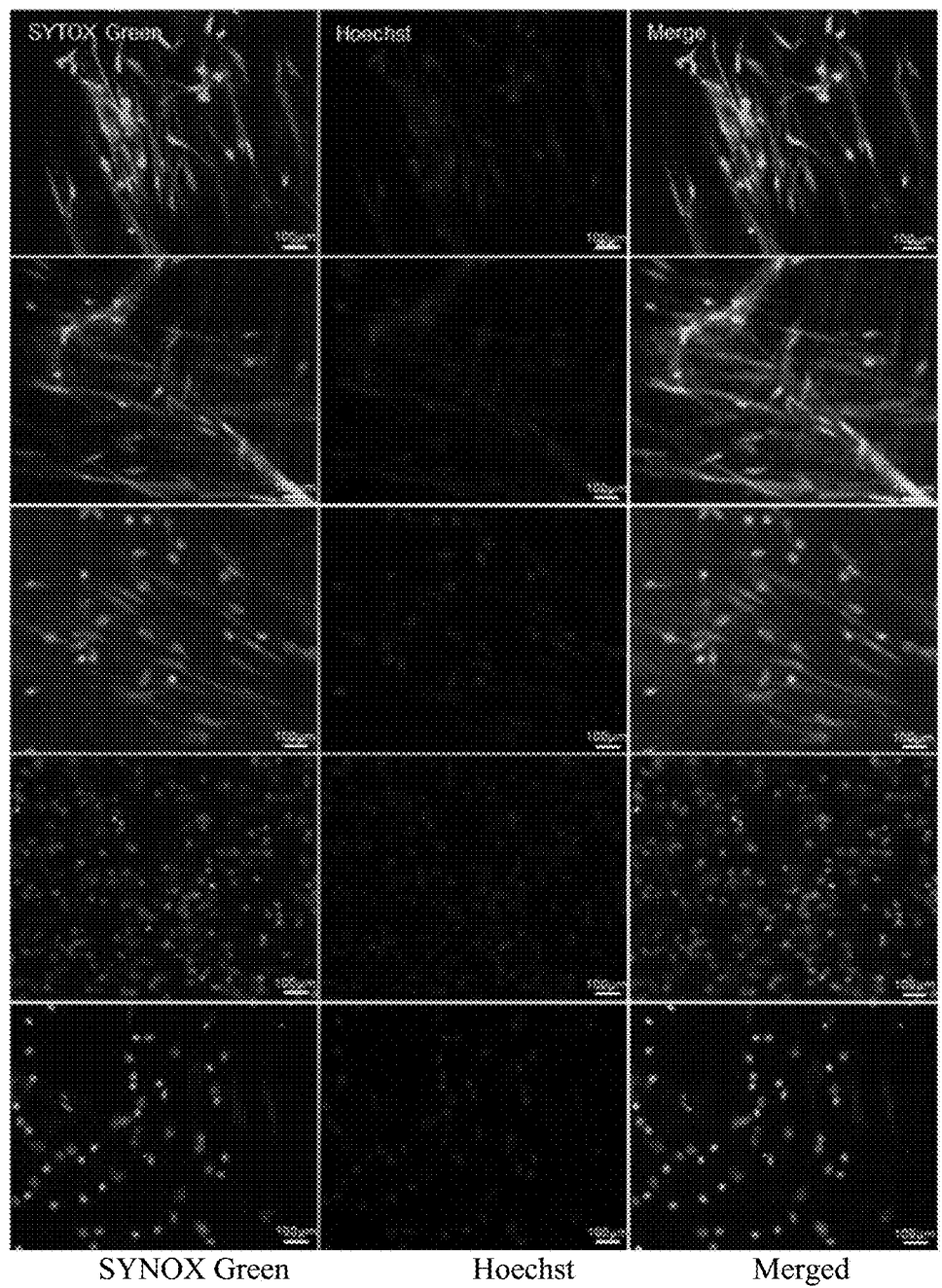
FIG. 5 is a photograph showing stimulated neutrophils produced inflammatory products (A, green staining strands) that were reduced by heparin in a dose dependent fashion.

Inflammatory and immunological ocular surface disease causes mucocellular aggregates. FIG. 4 is a photograph showing mucocellular aggregates contain of neutrophils (red stained cells) and their inflammatory and profibrotic products. Heparins reduced mucocellular aggregates and neutrophil inflammatory strands, therefore can reduce inflammation and fibrosis to prevent or treat symblepheron, subconjunctival fibrosis and fornix foreshortening and dry eye diseases.

Example 5

Stimulated neutrophils produce inflammatory products (A, green staining strands) that are reduced by heparin in a dose dependent fashion (from top to bottom: 0.01 IU/mL, 0.1 IU/mL, 1 IU/mL, 10 IU/mL, and 100 IU/mL, respectively). Heparin at 100 IU/ml reduces the amount of inflammatory strands of neutrophils almost completely.

Example 6

Figure 6:
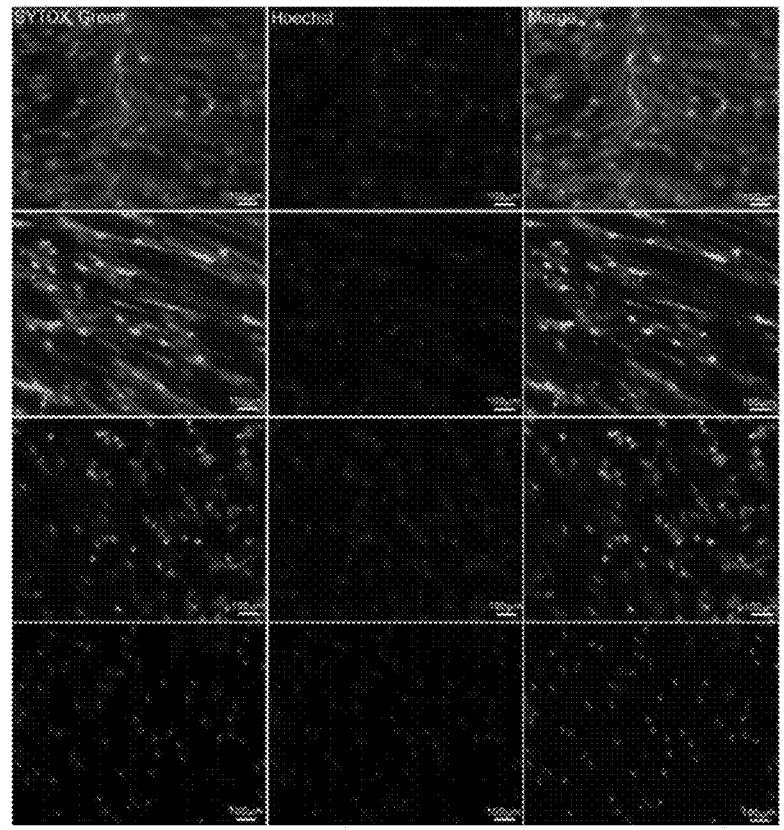
FIG. 6 is a photograph showing Enoxaparin (low molecular weight heparin) reduces neutrophil inflammatory products (green staining strands) in a dose dependent fashion.

Stimulated neutrophils produce inflammatory products (green staining strands) that were reduced by Enoxaparin (low molecular weight heparin) in a dose dependent fashion as shown in FIG. 6 (from top to bottom: 10 μg/mL, 20 μg/mL, 40 μg/mL, and 80 μg/mL, respectively). As can be seen in FIG. 6, Enoxaparin at 80 μg/mL reduced the inflammatory strands of neutrophils almost completely.

Example 7

Figure 7:
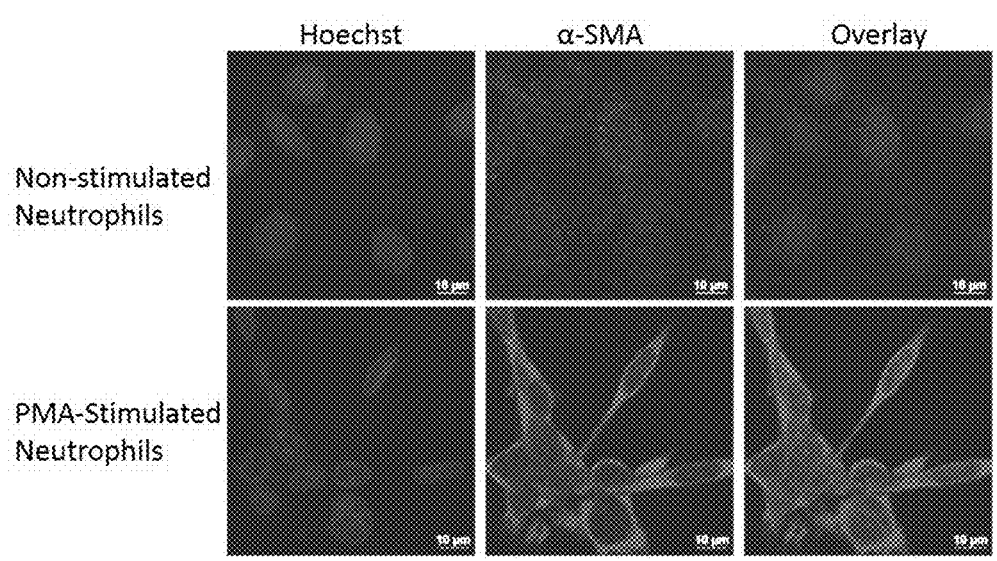
FIG. 7 is a photograph showing α-SMA antibody immunofluorescent staining (red) of human ocular surface epithelial cells that were incubated with/without inflammatory products of PMA-stimulated neutrophils.

Stimulated neutrophils produce inflammatory products that cause transition of epithelial cells to smooth muscle actin positive mesenchymal cells. As shown in FIG. 7, these α-SMA positive cells (red staining cells) contribute to symblepheron, subconjunctival fibrosis and fornix foreshortening in dry eye diseases. In this experiment, inflammatory products of PMA-stimulated neutrophils were incubated with human ocular surface epithelial cells. The epithelial cells transformed to myofibroblasts as evidenced by intense immunofluorescent staining with α-SMA antibody (red). Heparins reduce the neutrophil inflammatory strands, and therefore can reduce epithelial mesenchymal transition and fibrosis to prevent or treat symblepheron, subconjunctival fibrosis and fornix foreshortening in dry eye diseases.

Example 8

Figure 8:
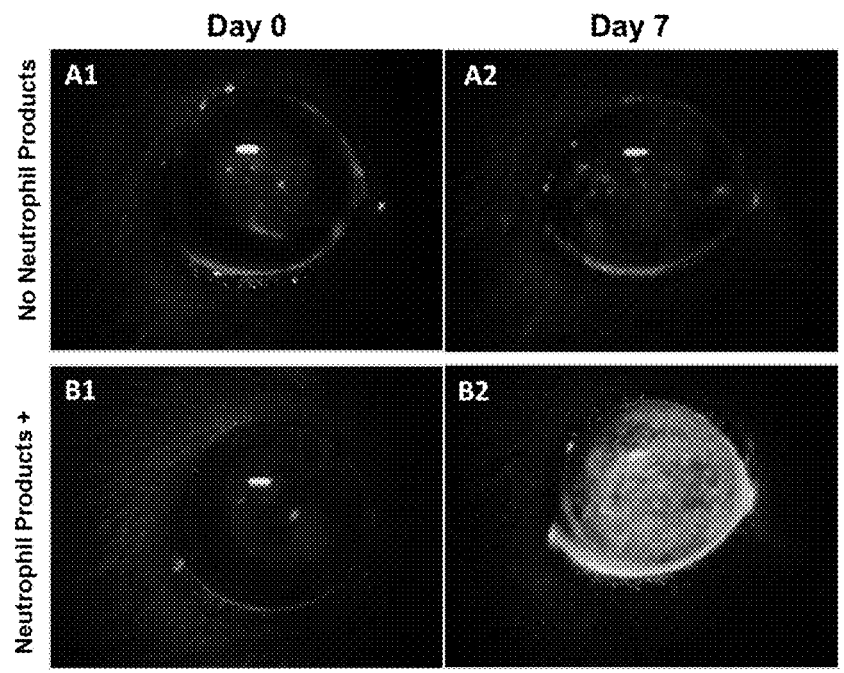
FIG. 8 is a photograph of fluorescein staining showing stimulated neutrophils produce inflammatory products in ocular surface disease.

Stimulated neutrophils produced inflammatory products that contributed to ocular surface disease. Supernatant from unstimulated neutrophils do not contain inflammatory strands, therefore as shown in FIG. 8 did not cause ocular surface disease (A1 at day 0 and A2 after 7 days of exposure to unstimulated neutrophil supernatant). Supernatant from stimulated neutrophils contain inflammatory strands, therefore did cause ocular surface disease (B1 at day 0 and B2 after 7 days of exposure to unstimulated neutrophil supernatant). Extensive fluorescein staining can be seen in B2 after exposure to neutrophil inflammatory products. Heparins reduced the amount of neutrophil inflammatory strands; therefore, it can reduce ocular surface disease and fibrosis.

Example 9

Figure 9A:
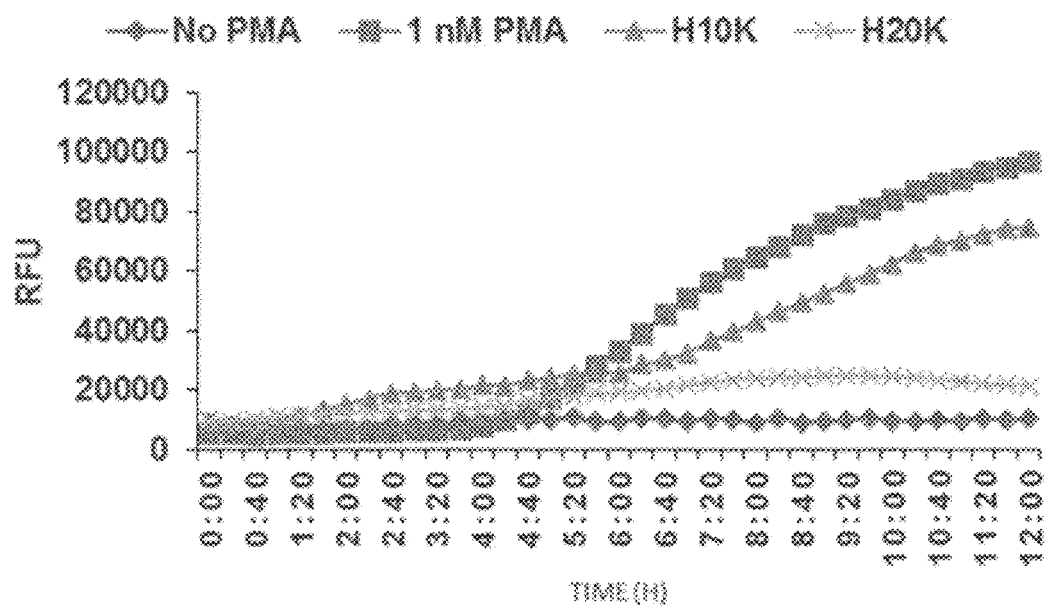
FIG. 9A is a graph of kinetic assay showing reduction in the amount of neutrophil inflammatory products by heparin in a dose dependent manner.
Figure 9B:
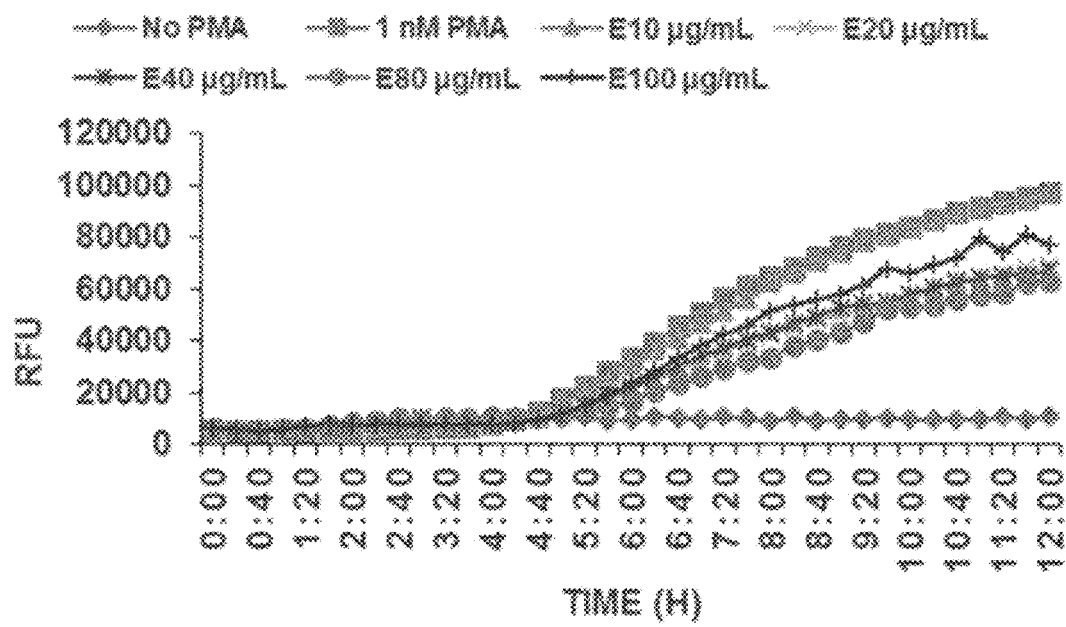
FIG. 9B is a graph of kinetic assay showing reduction in the amount of neutrophil inflammatory products by Enoxaparin in a dose dependent manner.

As shown in FIGS. 9A and 9B, kinetic assay showed that neutrophil inflammatory products are produced with stimulation by 1 nM PMA (squares). Heparin (FIG. 9A) and Enoxaparin (FIG. 9B) caused a dose dependent reduction in the amount of neutrophil inflammatory products that were produced with stimulation by 1 nM PMA. Results showed that reduction in production of neutrophil inflammatory products can be achieved by heparins and reduce inflammation and fibrosis.

Example 10

Experimental and clinical data showed that sub-anticoagulant dose heparin eye drops significantly reduced pain and discomfort in patients with dry eye disease (DED) and also reduced corneal epithelial disease and corneal inflammation. Thus, sub-anticoagulant dose of heparin eye drops (e.g., 100 IU/ml 2 to 3 times a day) are effective in treating DED and improving ocular surgery outcomes. Significantly, heparin eye drops caused resolution of corneal filaments and significantly reduced ocular pain and redness.

A 54 year old male developed ocular GVHD after bone marrow transplant. Clinical presentation included severe tear deficiency. Left eye developed multiple corneal filaments and ocular discomfort. Patient was unable to wear bandage contact lens because of ocular discomfort. He was using serum tear eye drops four times a day and methylprednisone eye drops 1% once a day with no relief. Heparin eye drops 100 IU/ml (sub-anticoagulant dose) was started three time a day. At follow up visit 2 weeks later, no corneal filaments were seen. The ocular pain intensity was described as 9/10 prior to starting heparin eye drops. After heparin eye drops use pain reduced significantly to 3/10. After Heparin eye drop use, eye redness reduced by 60%. Patient reported sleeping better at night.

Example 11

In this case heparin eye drops use resulted in significant reduction of ocular surface disease and ocular pain. A 53 year old female developed severe tear deficiency (Schirmer I=0 in both eyes) and severe ocular surface disease after bone marrow transplant for leukemia. Patient was using artificial tears, erythromycin ointment, steroid eye drops, doxycycline PO and scleral lens. Despite this aggressive treatment the patient was severely symptomatic (OSDI=67.5) and symptom intensity was 6/10 (distressing/miserable). Heparin eye drops 100 IU/ml twice a day was started and all other treatment was continued. Ocular symptoms interfered 'quite a bit' with patient's mood, enjoyment of life and socializing. Patient was followed up after 3 weeks. Patient was much more comfortable. Subjective global assessment was 'much improved'. OSDI reduced significantly to 19.4 and symptom intensity reduced to ²/10 (mildly annoying). Ocular symptoms did not interfere (not at all) with patient's mood, enjoyment of life and socializing. Corneal staining decreased significantly (50%) from ⁶/15 to ³/15. Conjunctival staining deceased significantly from ⁴/6 to ¹/6.

Example 12

In this case, heparin eye drops use resulted in reduction of post-surgical ocular surface fibrosis. A 57 year old female with severe tear deficient dry eye disease (DED) due to oGVHD developed symblepherons. In left eye, symblepheron was surgically incised which postoperatively caused excessive conjunctival scarring. There was inadequate resolution of conjunctival scarring with steroid eye drops and serum tears. Heparin eye drops (100 IU/ml three times a day) was started. After 8 weeks of heparin eye drop use, scar tissue was significantly reduced. Surrounding erythema (redness) and vascularization were also reduced.

Example 13

In this case heparin eye drops use resulted in reduction of post-surgical adherent inflammatory mucocellular aggregates. A 54 year old female underwent keratoprosthesis surgery. Postoperatively, significant amount of inflammatory mucocellular aggregate was adherent to the keratoprosthesis (around the corneal sutures and front plate). The optic (transparent plastic) of the keratoprosthesis was covered with mucocellular deposits. These mucocellular aggregates are composed of neutrophils and their inflammatory products hence can cause melting of corneal tissue and failure of surgery. Heparin 100 IU/ml was started three times a day. After 4 weeks of heparin use, the mucocellular aggregates were almost completely removed. The optic was also cleared of mucoid deposits.

Example 14

In this case heparin eye drops use resulted in reduction ocular surface disease and remarkable reduction of ocular eye pain. A 58 year old female with mixed mechanism DED (tear deficient dry eye disease with Meibomian gland dysfunction) presented with severe ocular discomfort (OSDI of 80.55) and symptom intensity of ⁹/10 (unbearable/excruciating). Patient was using erythromycin eye ointment, steroid eye drop and doxycycline PO. Despite this treatment, she was in extreme discomfort. Heparin eye drop 100 IU/ml three times a day was started. After 4 weeks of heparin eye drop use patient was significantly more comfortable. OSDI decreased to only 5. Symptom intensity reduced to 0 (none). Subjective global assessment was 'much improved'. Corneal staining also significantly reduced (50%) from ⁶/15 to ³/15. Superior conjunctival bulbar staining also reduced by 50%. Clinical global impression was "much improved".

Example 15

A 73 year old male with tear deficient DED due to oGVHD had significant mucocellular deposits over contact lens (soft and PROSE) causing blurring of vision. Heparin eye drops 100 IU/ml were started. After 4 weeks of heparin eye drop treatment, deposits over the contact lens were significantly reduced and patient's vision improved. Patient also reported improved comfort.

Example 16

Figure 10:
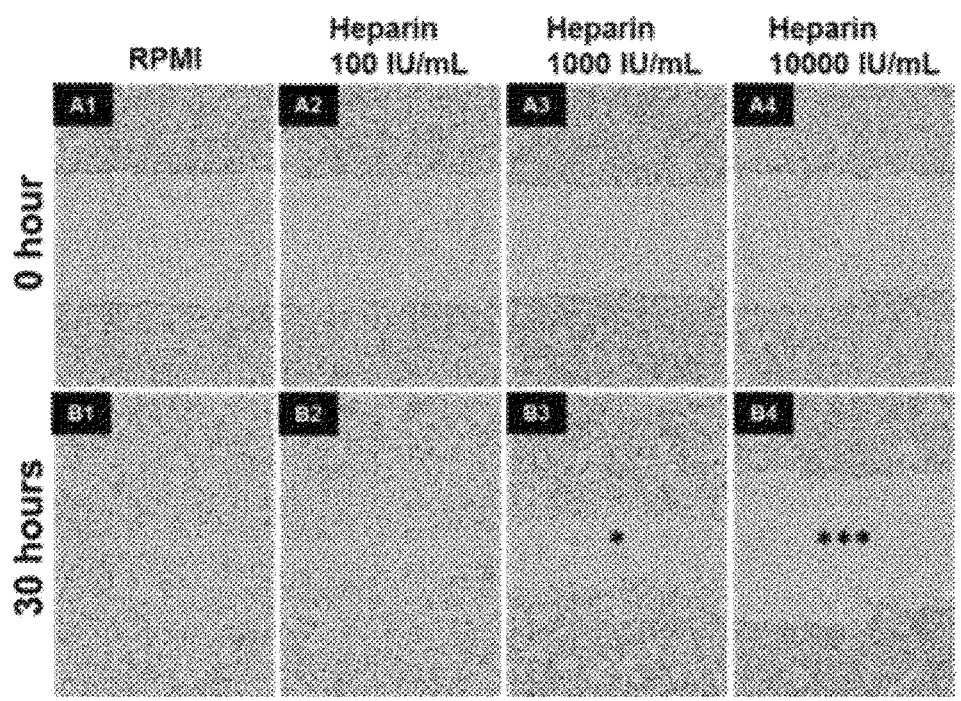
FIG. 10 is a photograph showing anticoagulant dose of heparin causes human corneal epithelial cell cytotoxicity whereas sub-anticoagulant dose of heparin does not cause cytotoxicity.
Figure 11:
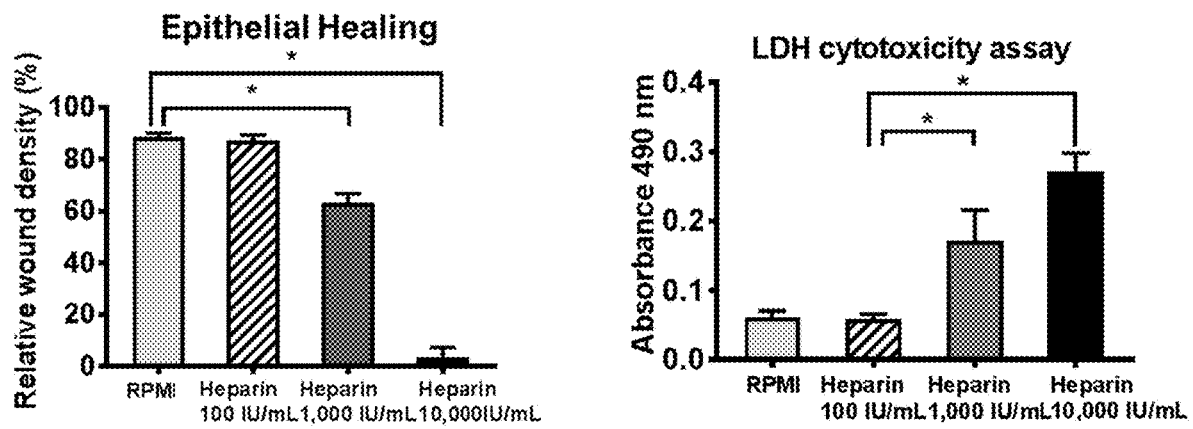
FIG. 11 is a bar graph of cytotoxicity assay showing that LDH was significantly higher with anticoagulant dose heparin (1000 and 10,000 IU/ml) as compared to control condition (culture media RPMI) and sub-anticoagulant heparin dose (100 IU/ml).

As shown in FIGS. 10 and 11, anticoagulant dose of heparin causes human corneal epithelial cell cytotoxicity whereas sub-anticoagulant dose of heparin does not cause cytotoxicity. In this experiment human corneal epithelial cells were grown to confluence and scratch wounds were made. Epithelial cell healing with sub-anticoagulant dose heparin (100 IU/ml) was similar to that of control condition (culture media RPMI) (FIG. 10 A1→B1 versus A2→B2). Epithelial cell healing with anticoagulant dose heparin (1000 and 10,000 IU/ml) was significantly delayed as compared to that of control condition (culture media RPMI) and sub-anticoagulant heparin dose (100 IU/ml). Cytotoxicity assay confirmed that LDH was significantly higher with anticoagulant dose heparin (1000 and 10,000 IU/ml) as compared to control condition (culture media RPMI) and sub-anticoagulant heparin dose (100 IU/ml). See FIG. 11. This experiment shows that sub-anticoagulant heparin is safe for human corneal epithelial cells whereas higher anti-coagulant doses are not safe.

Example 17

Sub-anticoagulant dose heparin (100 IU/ml) significantly reduced corneal epithelial disease and corneal inflammation in a murine model of neutrophil product (NETs) induced corneal disease. Neutrophil products (NETs) when applied to corneal surface induced epithelial disease and fluorescein staining. When Heparin was added to NETs, epithelial disease and fluorescein staining was significantly reduced. Protein levels of inflammatory cytokines were also determined (IL-lb and IP-10) using a Magpix platform. Heparin addition to NETs significantly reduced corneal abundance of IL-lb and IP-10.

Example 18

Figure 12:
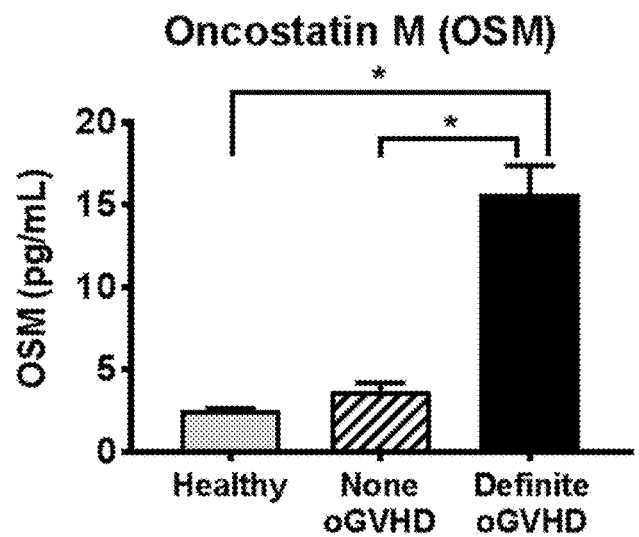
FIG. 12 is a bar graph showing patients with tear deficient DED, such as oGVHD, have excessive amounts of Oncostatin M (OSM) in the tear fluid.
Figure 13:
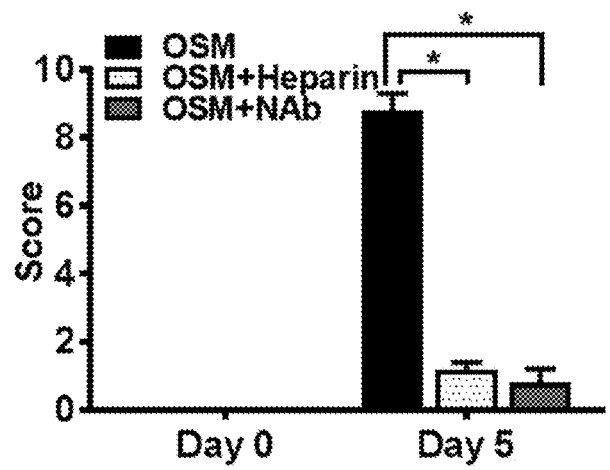
FIG. 13 is a bar graph showing corneal fluorescein staining induced by OSM was significantly reduced with addition of heparin (100 IU/ml) or antibody to OSM.

Patients with tear deficient DED, such as those occuring in oGVHD, were shown to have excessive amounts of Oncostatin M (OSM) in the tear fluid (FIG. 12). Excessive amounts of OSM can cause corneal epithelial disease similar to that seen in DED patients. Experiments were performed wherein recombinant OSM protein was applied to the mouse corneas that resulted in corneal epithelial disease. Addition of heparin to recombinant OSM significantly reduced the corneal disease as also the addition of neutralizing antibodies to OSM. FIG. 13 shows that corneal fluorescein staining induced by OSM was significantly reduced with addition of heparin (100 IU/ml) or neutralizing antibody to OSM. These data provide the rationale for combining inhibitors or OSM to Heparin eye drops to potentiate the beneficial effect of heparin in DED. OSM inhibitors used can be selected from neutralizing antibodies, neutralizing peptides and small molecules and other gene based approaches. These OSM inhibitors can be used independently as therapeutic proteins/peptides/small molecules for DED treatment.

Example 19

Experiments also showed that following combinations potentiate the beneficial actions of Heparin eye drops and these combinations can be used in DED: 1. Heparin plus inhibitors of oncostatin M (e.g. neutralizing antibodies); 2. Heparin plus inhibitors of LIGHT (e.g. neutralizing antibodies); 3. Heparin plus inhibitors of NGAL (e.g. neutralizing antibodies); and 4. Heparin plus DNase I.

Example 20

In this ex vivo experiment, mucocellular aggregates from a patient with severe tear deficient DED were collected, and stained with Hematoxylin-Eosin and Sytox Green to demonstrate their cellular and extracellular structure. The extracellular structures (green strands) were dissolved when treated with sub-anticoagulant heparin (100 IU/ml), but remained substantially intact when treated with only the culture media (RPMI). This result indicates heparin dissolves extracellular components of mucocellular aggregates in patients with tear deficient DED.

Example 21

In this experiment, heparin eye drops use resulted in remarkable reduction of ocular eye pain and mucocellular aggregated in a patient with cicatricial conjunctivitis. A 65 year old male was referred with complaints of chronic redness and constant irritation of both eyes. Patient was moderately symptomatic (OSDI=20.83) with symptom intensity of 4.5 (nagging/uncomfortable). His mood and enjoyment of life were somewhat affected by the eye symptoms. Tear production was normal (Schirmer I of 16 in right eye and 12 in left eye). Meibomian glands were normal. Ocular examination revealed considerable conjunctival subepithelial scarring in both upper eyelids. Patient was diagnosed with cicatricial conjunctivitis likely atopic. Heparin eye drops (100 IU/ml) tid was started. After four months of heparin use, examination reveals that patient's condition had improved. OSDI reduced from 20.8 to 5.0 and symptom intensity has reduced from 4.5/10 to 2/10. There was no affective interference due to the symptoms. Subjective Global Assessment revealed 'much improved' in both eyes. Patient reported that mucocellular aggregates and pain/grittiness had reduced by approximately 95%. Clinical Global Impression was 'moderate improvement' in both eyes.

Example 22

In this case heparin eye drops use resulted in reduction of ocular light sensitivity and corneal filaments in a patient with secondary Sjogren syndrome. A 37 year old female with rheumatoid arthritis and Sjogrens disease presented with corneal filaments in the left eye. Patient has severe tear deficient DED and was severely symptomatic (OSDI=56.8). symptom intensity was 4 (nagging/uncomfortable) in both eyes. Heparin 100 IU/ml three times a day was started. After one month of treatment with heparin eye drops, symptoms reduced considerably to mild (OSDI of 15) and symptom intensity reduced to 2 in both eyes (mildly annoying), Subjective global assessment was 'improved'. Slit lamp examination revealed no corneal filaments. Clinical global impression was 'moderate improvement.

Example 23

In this case, combined treatment with heparin eye drops and DNase I eye drops was more effective than heparin alone. A 55 year old male had severe tear deficiency (Schirmer I=0 mm in right eye and 1 mm in left eye). Patient was severely symptomatic (OSDI=95) and symptom intensity of 9/10 (intense/horrible). Patient also had extensive mucocellular deposits on the scleral contact lens that interfered with vision and quality of life. A combination treatment was started—Heparin eye drops 100 IU/ml tid and DNase I eye drops 1% tid. One month after treatment patient reported significant improvement in symptoms and reduction of mucocellular discharge. Patient noticed improvement with Heparin eye drops alone, but the improvement was best when both heparin and DNase I eye drops were used.

Example 24

In this case heparin eye drops use resulted in resolution of pseudomembranes in a patient with herpes virus infection of cornea and tear deficient DED. A 48 year old female had severe tear deficient dry eye disease (DED) due to oGVHD. She developed HSV keratitis—corneal dendritic lesions and a pseudomembrane formed in the lower eyelid. In addition to Acyclovir PO, Heparin eye drops were started 100 IU/ml tid. This treatment led to resolution of HSV keratitis corneal lesions and pseudomemberane.

Example 25

Figure 14:
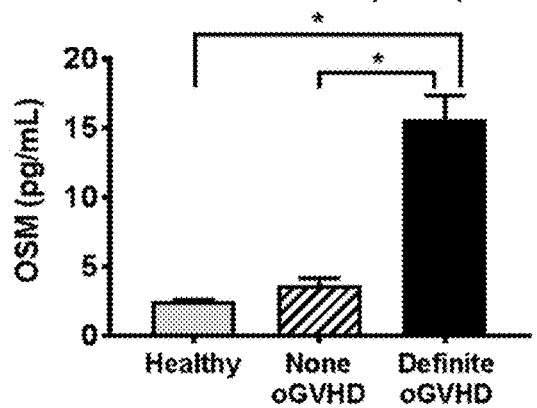
FIG. 14 is a graph showing oncostatin M (OSM) levels were significantly higher in ocular surface washings of definite oGVHD patients.
Figure 15:
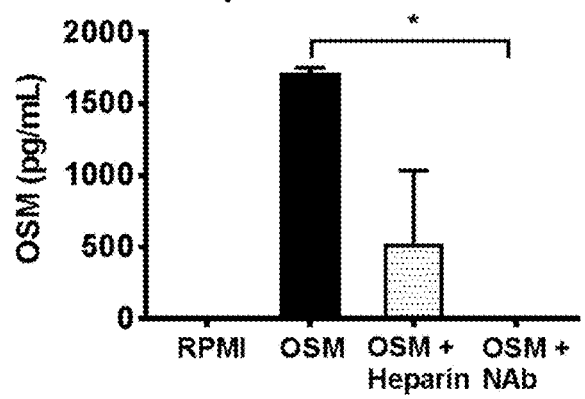
FIG. 15 is a graph showing both heparin and Neutralizing antibody (NAb) reduced OSM protein levels.

The molecular component of Neutrophil Extracellular Traps (NETs) that may cause epitheliopathy was investigated. Because oncostatin M (OSM) levels were significantly higher in ocular surface washings of definite oGVHD patients (FIG. 14), whether this NET component causes epitheliopathy was investigated. OSM was present in abundance in mucocellular aggregates (MCA) collected from definite oGVHD patients. OSM is a heparin binding protein, therefore incubation with heparin or Neutralizing antibody (NAb) reduced recombinant OSM protein levels (FIG. 15). In murine NETs, OSM is present in great abundance (614.67±95.73 pg/mL) and its levels are significantly reduced in heparinized NETs (19.95±0.00 pg/mL).

Figure 16:
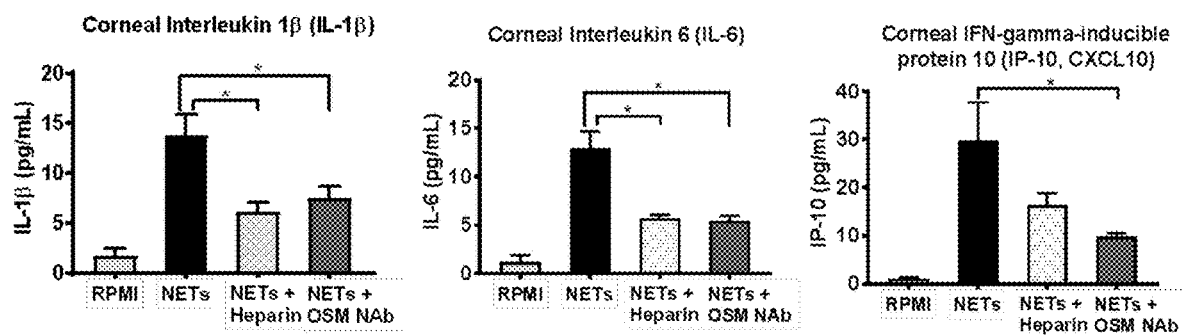
FIG. 16 is a graph showing corneas exposed to NETs had significantly higher abundance of various inflammatory cytokines compared to heparinized NETs and OSM NAb incubated NETs.

Whether reducing OSM levels in naive NETs using heparin or OSM NAb abrogates NETs induced epitheliopathy in murine corneas was investigated. Naive NETs, heparinized NETs and OSM NAb incubated NETs was applied to naïve murine corneas for five consecutive days. Significantly greater corneal fluorescein staining was observed at Day 5 following application of NETs (7.20±0.97; p<0.05) as compared to heparinized NETs (0.80±0.49) and OSM NAb incubated NETs (0.40±0.24). At Day 5, corneas were excised and abundance of inflammatory cytokines (IL-1β, IL-6 and IP-10) were determined in lysates. Corneas exposed to NETs had significantly higher abundance of these inflammatory cytokines as compared to heparinized NETs and OSM NAb incubated NETs. FIG. 16.

In addition, whether OSM recombinant protein can produce epitheliopathy similar to NETs and whether reducing OSM levels using heparin or OSM NAb abrogates that effect was also investigated. Significantly greater corneal fluorescein staining was observed at Day 5 following application of OSM (8.75±0.48; p<0.05) compared to OSM incubated with heparin (1.20±0.20) and OSM incubated with OSM NAb (0.80±0.37). These experiments indicate that NETs cause corneal epitheliopathy possibly due to presence of OSM and epitheliopathy can be prevented with heparin. To test this theory, a patient with oGVHD who had corneal and conjunctival epitheliopathy was treated with heparin eye drop (100 IU/mL) three times a day for four weeks. A significant reduction in corneal and conjunctival epitheliopathy was observed.

Example 26

T-cell activation and proliferation are well recognized to play an important role in chronic GVHD pathophysiology.

Figure 17A:
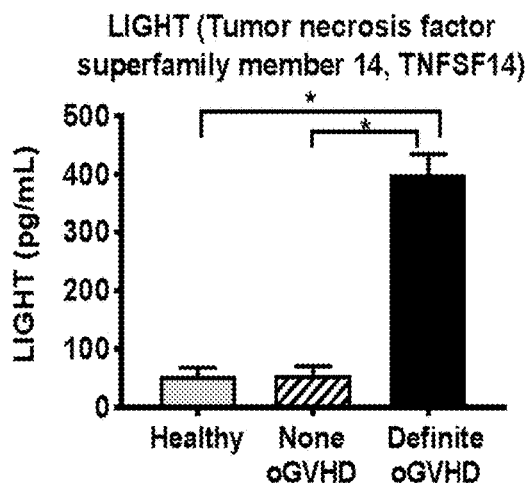
FIG. 17A is a graph of LIGHT levels in ocular surface washings of healthy, none oGVHD and definite oGVHD patients.
Figure 17B:
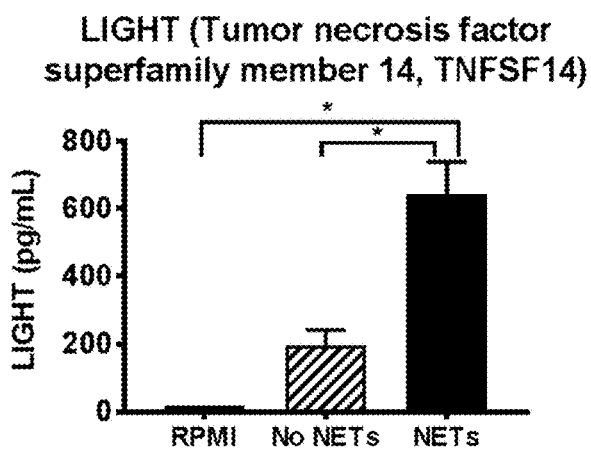
FIG. 17B is a graph of LIGHT in experimental NETs of Example 26.
Figure 18:
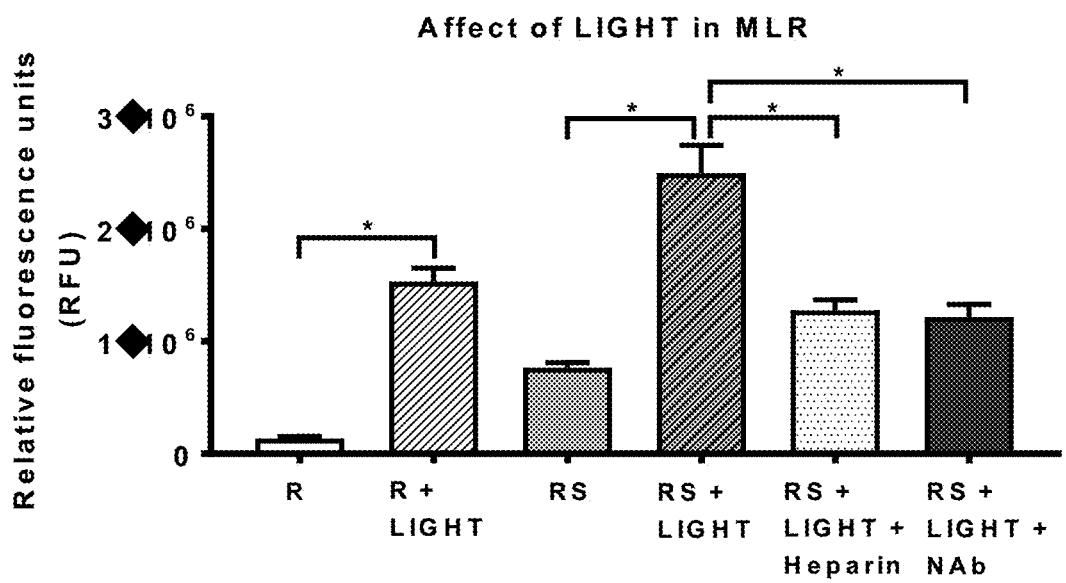
FIG. 18 is a graph showing the effect of the presence of heparin or LIGHT NAb in the amount of LIGHT protein present in MLR.

Therefore, whether NETs can affect T-cell proliferation in a mixed lymphocytic reaction (MLR) was investigated. First, MCA was immunostained with CD3 antibody to demonstrate the presence of T-cells in close proximity to NETs. CD3 positive T-cells were seen in 42% of 12 MCAs examined. Next, a MLR was performed using lymphocytes from two different healthy subjects to simulate an alloreaction. Addition of naive NETs resulted in significantly increased proliferation in MLR ($1.95 \times 10^6 \pm 1.31 \times 10^5$ RFU; $p<0.05$) whereas addition of heparinized NETs resulted in significantly lower MLR proliferation ($4.74 \times 10^5 \pm 4.11 \times 10^4$). Next, the molecular component of NETs that may have caused MLR proliferation was investigated. Because LIGHT levels were significantly higher in ocular surface washings of definite oGVHD patients (FIG. 17A) and LIGHT was present in abundance in experimental NETs (FIG. 17B), whether this NET component causes immunoproliferation was investigated. First, MCA with LIGHT antibody was immunostained and demonstrated the presence of LIGHT protein in neutrophil cytoplasm and extracellularly. Next, the effect of LIGHT protein in MLR was investigated. Addition of LIGHT to the MLR resulted in significantly increased proliferation ($2.49 \times 10^6 \pm 2.49 \times 10^5$ RFU; $p<0.05$) whereas addition of LIGHT with either heparin or LIGHT NAb resulted in significantly lower MLR proliferation ($1.22 \times 10^6 \pm 1.11 \times 10^5$ RFU). FIG. 18. Compared to naive NETs, when NETs were added to MLR with LIGHT NAb, proliferation was significantly reduced ($4.87 \times 10^5 \pm 3.43 \times 10^4$ RFU; $p<0.05$). These data show that NETs or recombinant LIGHT increase MLR proliferation whereas addition of heparin or LIGHT NAb reduces it, indicating that LIGHT may cause immunoproliferation which can be suppressed with heparin.

Example 27

Figure 19A:
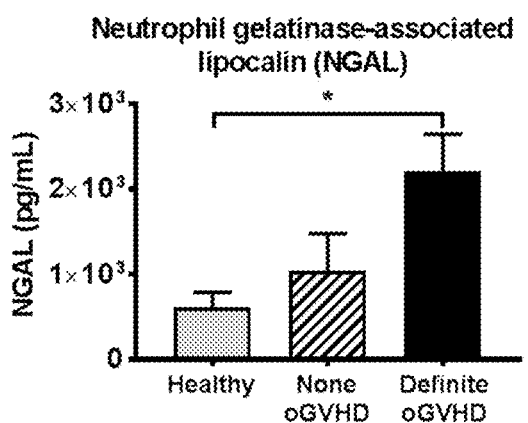
FIG. 19A is a graph of NGAL levels in ocular surface washings of healthy, none oGVHD and definite oGVHD patients.
Figure 19B:
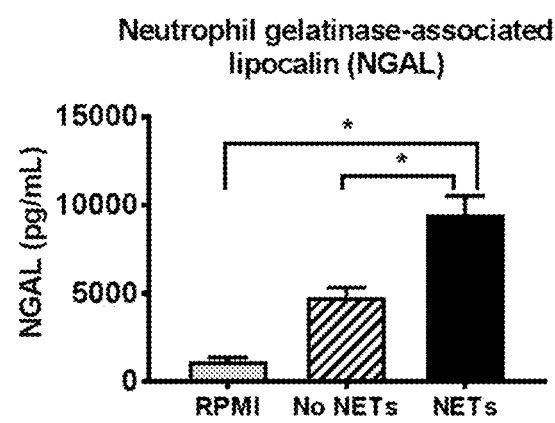
FIG. 19B is a graph of NGAL in experimental NETs of Example 27.

Meibomian gland disease is a conspicuous feature of oGVHD. As compared to normal meibomian gland, patients with oGVHD have extensive atrophy or truncation of meibomian glands. Meiboscale in oGVHD patients is significantly greater ($2.07 \pm 0.19$; $p<0.05$) compared to healthy subjects or patient with none oGVHD. Because NGAL levels were significantly higher in ocular surface washings of definite oGVHD patients ($2212.00 \pm 430.71$; $p<0.05$) (FIG. 19A) and NGAL was present in abundance in experimental NETs ($9475.34 \pm 1052.84$; $p<0.05$) (FIG. 19B), whether this NET component effects of meibomian gland differentiation and proliferation was investigated. MCA was immunostained with NGAL antibody and demonstrated the presence of NGAL protein in neutrophil cytoplasm and extracellularly. To determine the effect of NETs on meibomian glands, immortalized meibomian gland epithelial cells were cultivated and differentiated. Lipid accumulation was detected using LipidTOX staining. The fluorescence intensity of LipidTox Green neutral lipid stain was significantly higher in differentiation medium (DFM) ($24.92 \pm 1.21$ A.U; $p<0.05$) as compared to serum free medium (KSFM, Keratinocyte serum free medium) ($6.93 \pm 0.57$ A.U). Addition of NETs to DFM medium significantly decreased the accumulation of lipids ($7.60 \pm 0.85$ A.U; $p<0.05$). In contrast, addition of heparinized NETs to DFM medium did not reduce accumulation of lipids ($33.98 \pm 2.18$ A.U). The reduction in lipid accumulation with NETs was abrogated with addition of NGAL NAb ($21.21 \pm 0.83$ A.U). Similar to NETs, addition of rNGAL to DFM medium significantly decreased the accumulation of lipids ($10.88 \pm 0.35$ A.U). The reduction of lipid accumulation with rNGAL was abrogated with addition of NGAL NAb ($17.82 \pm 0.43$ A.U) and heparin ($15.66 \pm 1.72$ A.U).

Figure 20:
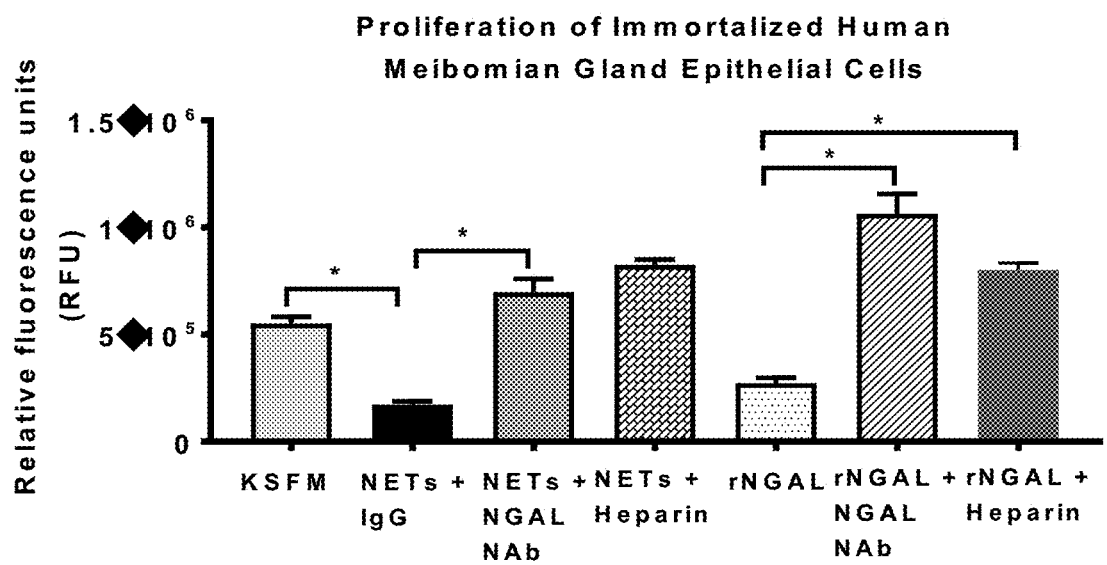
FIG. 20 is a graph showing the effect of NGAL on proliferation of human meibomian gland (MG) cells.

Next, the effect of NGAL on proliferation of human MG cells was investigated. Compared to control KSFM medium ($5.52 \times 10^5 \pm 3.11 \times 10^4$ RFU), addition of NETs to KSFM medium significantly reduced meibomian gland proliferation ($1.72 \times 10^5 \pm 1.58 \times 10^4$ RFU; $p<0.05$). FIG. 20. The reduction of MG cell proliferation with NETs was abrogated with addition of NGAL NAb ($6.98 \times 10^5 \pm 6.18 \times 10^4$ RFU) and heparin ($8.25 \times 10^5 \pm 2.56 \times 10^4$ RFU). Similar to NETs, addition rNGAL to KSFM medium significantly decreased MG cell proliferation. The reduction of MG cell proliferation with rNGAL was abrogated with addition of NGAL NAb and heparin. These data show that NETs or recombinant NGAL significantly reduce MG cell proliferation and differentiation whereas addition of heparin or NGAL NAb abrogates this reduction, suggesting that NGAL (a molecular component of NETs) may cause MG cell dysfunction which can be suppressed with heparin.

Example 28

Figure 21A:
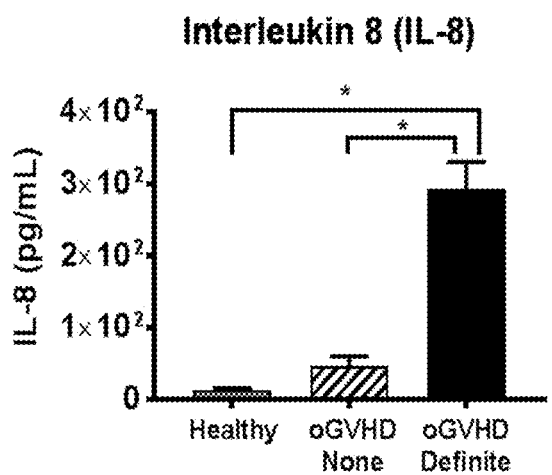
FIG. 21A is a graph showing IL-8 levels in ocular surface washings of definite oGVHD patients.
Figure 21B:
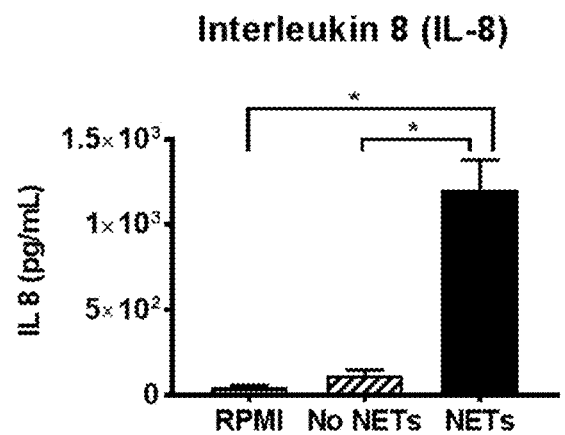
FIG. 21B is a graph showing IL-8 levels in experimental NETs.

This example determines the amount of IL-8 in patients with ocular surface disease. The level of IL-8 was significantly higher in ocular surface washings of definite oGVHD patients (FIG. 21A) and IL-8 was present in abundance in experimental NETs (FIG. 21B).

The foregoing discussion of the invention has been presented for purposes of illustration and description. The foregoing is not intended to limit the invention to the form or forms disclosed herein. Although the description of the invention has included description of one or more embodiments and certain variations and modifications, other variations and modifications are within the scope of the invention, e.g., as may be within the skill and knowledge of those in the art, after understanding the present disclosure. It is intended to obtain rights which include alternative embodiments to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter. All references cited herein are incorporated by reference in their entirety.

What is claimed is:

1. A method for relieving or arresting a clinical condition or disease selected from the group consisting of inflammatory and immunological ocular surface disease that causes symptoms of ocular discomfort, mucocellular aggregates/debris in tear film, symblepheron formation, fornix foreshortening, eyelid margin/conjunctival keratinization, said method comprising administering directly to an ocular surface of a patient in need of such a treatment an ophthalmic formulation consisting of a therapeutically effective amount of heparin and one or more pharmaceutically acceptable ophthalmic excipients, wherein said clinical condition is selected from the group consisting of ocular graft-versus-host disease (oGVHD), Steven Johnson syndrome, ocular cicatricial pemphigoid (OCP), mild, moderate and severe tear deficient dry eye disease (DED), meibomian gland disease, superior limbic keratoconjunctivitis (SLK), tear sufficient DED, floppy eyelid syndrome, neurotrophic eye disease, aniridia, or a postoperative/post-trauma ocular condition, and wherein said postoperative/post-trauma ocular condition is selected from the group consisting of an ocular condition associated with post-ocular surface reconstruction surgery, antimetabolite application to eye surface, pterygium surgery, glaucoma surgery, keratoprosthesis surgery or radiation injury.

2. The method of claim 1, wherein said heparin comprises a coagulant heparin, a non-coagulant heparin, a heparin oligosaccharide or a combination thereof.

3. The method of claim 2, wherein said coagulant heparin comprises unfractionated heparin, a low molecular weight heparin, an ultra-low molecular weight heparin or a combination thereof.

4. The method of claim 2, wherein said non-coagulant heparin comprises a sulfation modified heparin, a glycol-split heparin, glycol-split N-acetylated heparin, other heparin derivative, or a combination thereof.

5. The method of claim 4, wherein said other heparin derivative comprises an N-acetylated heparin.

6. The method of claim 1, wherein said heparin is present from about 10 IU/mL to about 1000.

* * * * *